US008728823B2

(12) United States Patent
Lam et al.

(10) Patent No.: US 8,728,823 B2
(45) Date of Patent: May 20, 2014

(54) METHODS FOR DETECTING LUNG CANCER AND MONITORING TREATMENT RESPONSE

(75) Inventors: Stephen Lam, Vancouver (CA); John Yee, Vancouver (CA); Michael Kuzyk, Victoria (CA); Don Sin, Vancouver (CA); Marianne Dorthy Sadar, West Vancouver (CA); Carl Martin Tammemagi, Toronto (CA)

(73) Assignee: British Columbia Cancer Agency Branch, Vancouver, British Columbia (CA)

( * ) Notice: Subject to any disclaimer, the term of this patent is extended or adjusted under 35 U.S.C. 154(b) by 405 days.

(21) Appl. No.: 12/743,042

(22) PCT Filed: Nov. 24, 2008

(86) PCT No.: PCT/CA2008/002070
§ 371 (c)(1),
(2), (4) Date: May 14, 2010

(87) PCT Pub. No.: WO2009/065230
PCT Pub. Date: May 28, 2009

(65) Prior Publication Data
US 2010/0248290 A1 Sep. 30, 2010

Related U.S. Application Data

(60) Provisional application No. 60/989,914, filed on Nov. 23, 2007, provisional application No. 61/079,780, filed on Jul. 10, 2008.

(51) Int. Cl.
*G01N 33/00* (2006.01)
*G01N 33/566* (2006.01)

(52) U.S. Cl.
USPC .............................. 436/86; 436/63; 436/501

(58) Field of Classification Search
USPC ............................................. 436/86, 63, 501
See application file for complete search history.

(56) References Cited

FOREIGN PATENT DOCUMENTS

WO 2006/022895 A2 3/2006

OTHER PUBLICATIONS

Deutsch et al. Megakaryocyte Maturation is Associated With Expression of the CXC Chemokine Connective Tissue-Activating Peptide CTAP III; British Journal of Haematology, vol. 111 (2000) pp. 1180-1189.*
Fedorovych et al. Serum Haptoglobin in Lung Cancer Patients; Ukr. Biokhim. Zh. vol. 67, No. 2 (1995) pp. 103-105. Abstract only downloaded from http://www.ncbi.nlm.nih.gov/pubmed/8592775 on Oct. 31, 2012.*
MacCarter et al., "Connective tissue activation. XXIII. Increased plasma levels of a platelet growth factor (CTAP-III) in patients with rheumatic diseases", Clinica Chimica Acta., vol. 115, Sep. 10, 1981, pp. 125-134.
Castor et al., "Factors Modifying DNA Synthesis by Lung Fibroblasts in Vitro", Proceedings of the Society for Experimental Biology and Medicine, vol. 171, Jan. 1, 1982, pp. 109-113.
Yee et al., "Connective Tissue-Activating Peptide III: A Novel Blood Biomarker for Early Lung Cancer Detection", Journal of Clinical Oncology, Jun. 10, 2009, vol. 27, No. 17, pp. 2787-2792.
European Patent Application No. 08852226.3, Supplemental Search Report dated Nov. 16, 2010.
Hoogewerf et al., "CXC Chemokines Connective Tissue Activating Peptide-III and Neutrophil Activating Peptide-2 are Heparin/Heparan Sulfate-degrading Enzymes" The Journal of Biological Chemistry, Feb. 17, 1995, pp. 3268-3277, vol. 270, No. 7.
International Application No. PCT/CA2008/002070: International Search Report dated Feb. 24, 2009.
Maheshwari A, Christensen RD, Calhoun DA."ELR+ CXC chemokines in human milk". Cytokine 24(3):91-102, Jul. 2003.
Jemal A, et al. "Cancer statistics, 2007". CA Cancer J Clin 57, 43-66, Jan. 2007.
Parkin DM, et al. "Global cancer statistics, 2002". CA Cancer J Clin 55:74-108, Mar. 2005.
Rami-Porta R, et al. "The IASLC Lung Cancer Staging Project: proposals for the revision of the T descriptors in the forthcoming (seventh) edition of the TNM classification for lung cancer". J Thorac Oncol 2:593-602, Jul. 2007.
Henschke CI, et al. "Survival of patients with stage I lung cancer detected on CT screening". N Engl J Med 355:1763-1771, Oct. 2006.
McWilliams AM, et al. "Lung cancer screening using multi-slice thin-section computed tomography and autofluorescence bronchoscopy". J Thorac Oncol 1: 61-68, Jan. 2006.
Bach PB, et al. "Variations in lung cancer risk among smokers". J Natl Cancer Inst, 95: 470-478, Mar. 2003.

(Continued)

*Primary Examiner* — Susan Hanley
*Assistant Examiner* — Paul Martin
(74) *Attorney, Agent, or Firm* — Gail C. Silver; Borden Ladner Gervais LLP

(57) ABSTRACT

A method is described for detecting lung cancer comprising detecting an elevated level of a CTAP III-related biomarker in a biological sample from a subject at risk for developing lung cancer. Further, a method is described for predicting risk of developing lung cancer in a subject comprising detecting an elevated level of a CTAP III-related biomarker in a biological sample from a subject. Additionally, a method of monitoring the success of lung cancer treatment is described comprising detecting levels of a CTAP III-related biomarker in a biological sample from a subject undergoing treatment for lung cancer for comparison with a previous level obtained from the subject. Multivariate analysis may be incorporated into these methods, evaluating such clinical, or demographic risk factors as age, sex, smoking history, smoking status, smoking family history, education level, COPD, socio-economic status, body mass index and lung function. Kits for conducting such methods are described.

18 Claims, 13 Drawing Sheets

(56) References Cited

OTHER PUBLICATIONS

McWilliams AM, et al. "Innovative molecular and imaging approaches for the detection of lung cancer and its precursor lesions". Oncogene 21:6949-6959, 2002.

McWilliams AM, et al. "Lung cancer screening: a different paradigm". Am J Respir Crit Care Med, 168:1167-1173, Jul. 2003.

Gao WM, et al. "Distinctive serum protein profiles involving abundant proteins in lung cancer patients based upon antibody microarray analysis". BMC Cancer 5:110, Aug. 2005.

Khan N, et al. "Clinical utility of serum amyloid A and macrophage migration inhibitory factor as serum biomarkers for the detection of nonsmall cell lung carcinoma". American Cancer Society 101: 379-384, Jun. 2004.

Patz EF Jr, et al. "Panel of serum biomarkers for the diagnosis of lung cancer". J Clin Oncol 25:5578-5583, Dec. 2007.

Jacobs JM, et al. "Utilizing human blood plasma for proteomic biomarker discovery". J Proteome Res 4:1073-1085, May 2005.

Rifai N, et al. "Protein biomarker discovery and validation: the long and uncertain path to clinical utility". Nat Biotechnol 24:971-983, Aug. 2006.

Anderson NL, et al. "The human plasma proteome: history, character, and diagnostic prospects". American Society Biochemical 1: 845-867, Oct. 2002.

Anthonisen NR, et al. "The effects of a smoking cessation intervention on 14.5-year mortality: a randomized clinical trial". Ann Intern Med 142:233-239; Feb. 2005.

Man SF, et al. "C-reactive protein and mortality in mild to moderate chronic obstructive pulmonary disease". Thorax 61:849-853, May 2006.

Ahmed N, et al. "Proteomic-based identification of haptoglobin-1 precursor as a novel circulating biomarker of ovarian cancer". Br J Cancer 91:129-140, Jun. 2004.

Benson MD, et al. "Serum amyloid A in carcinoma of the lung". Cancer 57:1783-1787, Jul. 1985.

Liu DH, et al. "Serum amyloid A protein: a potential biomarker correlated with clinical stage of lung cancer". Biomed Environ Sci, 20: 33-40, 2007.

Yildiz PB, et al. "Diagnostic accuracy of MALDI mass spectrometric analysis of unfractionated serum in lung cancer". J Thorac Oncol 2:893-901, Oct. 2007.

Yang SY, et al. "Application of serum SELDI proteomic patterns in diagnosis of lung cancer". BMC Cancer 5: 83, Jul. 2005.

Prentice RL, et al. "The analysis of failure times in the presence of competing risks". Biometrics 34: 541-554, Dec. 1978.

Wasswa-Kintu S, et al. "Relationship between reduced forced expiratory volume in one second and the risk of lung cancer: a systematic review and meta-analysis". Thorax 60:570-575, Apr. 2005.

Strieter RM, et al. "Cancer CXC chemokine networks and tumour angiogenesis". Eur J Cancer 42:768-778, Jan. 2006.

Zhong L, et al. "Identification of secreted proteins that mediate cell-cell interactions in an in vitro model of the lung cancer microenvironment". Cancer Res 68:7237-45, Sep. 2008.

Arenberg DA, et al. "Epithelial-neutrophil activating peptide (ENA-78) is an important angiogenic factor in non-small cell lung cancer". J Clin Invest 102:465-72, Aug. 1998.

Chen JJ, et al. "Up-regulation of tumor interleukin-8 expression by infiltrating macrophages: its correlation with tumor angiogenesis and patient survival in non-small cell lung cancer". Clin Cancer Res 9:729-37, Feb. 2003.

Gewirtz AM, et al. "Chemokine regulation of human megakaryocytopoiesis". Blood 86:2559-2567, Oct. 1995.

Brandt E, et al. "Platelet-derived CXC chemokines: Old players in new games". Immunol Rev 177:204-16, 2000.

Iida N, et al. "Leukocyte-derived growth factor links the PDGF and CXC chemokine families of peptides". FASEB J 10:1336-1345, Sep. 1996.

Pillai MM, et al. "Monocyte-derived CXCL7 peptides in the marrow microenvironment". Blood 107:3520-3526, May 2006.

Hoogewerf AJ, et al. "CXC chemokines connective tissue activating peptide-III and neutrophil activating peptide-2 are heparin/heparan sulfate-degrading enzyme". J Biol Chem 3268-77, Feb. 1995.

Tang Z, et al. "Increased invasion through basement membrane by CXCL7—transfected breast cells". Am J Surg 196:690-696, Aug. 2008.

Kannel WB, et al. "A General cardiovascular risk profile: the Framingham Study". Am J Cardiol 38:46-51, Jul. 1976.

Diamond DL, et al. "Detection of beta-defensins secreted by human oral epithelial cells". J Immunol Methods 256:65-76, Jun. 2001.

Xiao Z, et al. "Generation of a baculovirus recombinant prostate-specific membrane antigen and its use in the development of a novel protein biochip quantitative immunoassay". Protein Expr Purif 19:12-21, Nov. 1999.

Le L, et al. "Identification of serum amyloid A as a biomarker to distinguish prostate cancer patients with bone lesions". Clin Chem 51:695-707, Jan. 2005.

Smith C, et al. "Increased levels of neutrophil-activating peptide-2 in acute coronary syndromes: possible role of platelet-mediated vascular inflammation". J Am Coll Cardiol 48(8):1591-9, Oct. 2006.

European Patent Application No. 08852226.3 Office Action dated Nov. 21, 2013.

\* cited by examiner

METHODS FOR DETECTING LUNG CANCER AND MONITORING TREATMENT RESPONSE

CROSS REFERENCE TO RELATED APPLICATIONS

This application claims the benefit of priority of U.S. Provisional Patent Application No. 60/989,914 filed Nov. 23, 2007, and U.S. Provisional Patent Application No. 61/079,780 filed Jul. 10, 2008 each of which is incorporated herein by reference in its entirety.

FIELD OF THE INVENTION

The present invention relates generally to methods of detecting lung cancer and methods for monitoring lung cancer treatment response.

BACKGROUND OF THE INVENTION

Lung cancer is the most common cause of cancer deaths worldwide with more than 1.2 million people dying of the disease each year[1,2]. Only 16% of lung cancer patients survive 5 years or more because the majority of the patients are diagnosed with advanced incurable disease by the time they present with symptoms[3]. This is in marked contrast to the 5 year survival of 70-90% that can be achieved when lung cancer is diagnosed and treated at an earlier stage[3-5]. Early detection and treatment of lung cancer is a promising strategy to reduce lung cancer mortality.

Technologies such as spiral computed tomography (CT), autofluorescence bronchosocopy (AFB), and optical coherence tomography are already available and can detect lung cancers down to the sub-millimeter range[6,7]. Although these sophisticated technologies are very sensitive, they are not specific enough to allow practical or cost-effective application in identifying early lung cancer in the general population, or even in high-risk sub-groups because there is wide variation in lung cancer risk even among heavy smokers[8]. If we can apply a filter to identify smokers at the highest risk for lung cancer, the positive predictive value of screening tests such as spiral CT can be significantly improved [9,10].

Spiral CT is very sensitive but the false-positive rate is relatively high resulting in unnecessary or potentially harmful downstream investigations and/or treatment. Bronchoscopy under conscious sedation can detect early lung cancer in the central airways not visible by spiral CT and can allow cytologic, histologic or genomic diagnosis of lung cancer. However, it is comparatively more expensive and time consuming than spiral CT. In the context of a health care delivery system, these technologies need be used in a selective fashion.

A blood based biomarker is attractive as a filter because blood is easily accessible and measurements may be repeated over time. Several studies have identified potential proteomic biomarkers that are differentially expressed between patients with and without lung cancer[11-13]. No biomarker has yet been validated in screen-detected early lung cancers. Major impediments in the discovery of biomarkers for detection of asymptomatic lung cancer have included measurement of thousands of proteins simultaneously in tens of samples, resulting in false positives; 2) use of analytical methods that do not provide precise and accurate determination of potential tumor specific proteins that are expressed in much lower concentrations than other more abundant proteins resulting in false negatives[14,15,16] and 3) a lack of access to blood samples collected in population based studies prior to clinical diagnosis of cancer for validation and replication.

There is an unmet need in the field for rapid, sensitive and accurate blood-based screening tests for the early detection of lung cancer, assessment of risk of developing lung cancer, and the monitoring of response after treatment with curative intent.

SUMMARY OF THE INVENTION

It is an object of the present invention to provide a method for detection of lung cancer, or to provide a method for monitoring treatment response.

In a first aspect, there is provided a method for detecting lung cancer comprising detecting an elevated level of a CTAP III-related biomarker in a biological sample from a subject at risk for developing lung cancer.

Further, there is provided a method of predicting risk of developing lung cancer in a subject comprising detecting an elevated level of a CTAP III-related biomarker in a biological sample from a subject.

Additionally, a method is provided for monitoring the success of lung cancer treatment with curative intent, comprising detecting levels of a CTAP III-related biomarker in a biological sample from a subject undergoing treatment for lung cancer for comparison with the a previous level obtained from the subject.

Further, a kit is provided for detecting risk of developing lung cancer comprising reagents for detecting an elevated level of a CTAP III-related biomarker in a biological sample from a subject at risk for developing lung cancer, together with instructions for use.

In a further aspect, there is described herein an imaging agent for detecting lung cancer comprising an antibody against CTAP III.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures.

DETAILED DESCRIPTION

Figure 1:
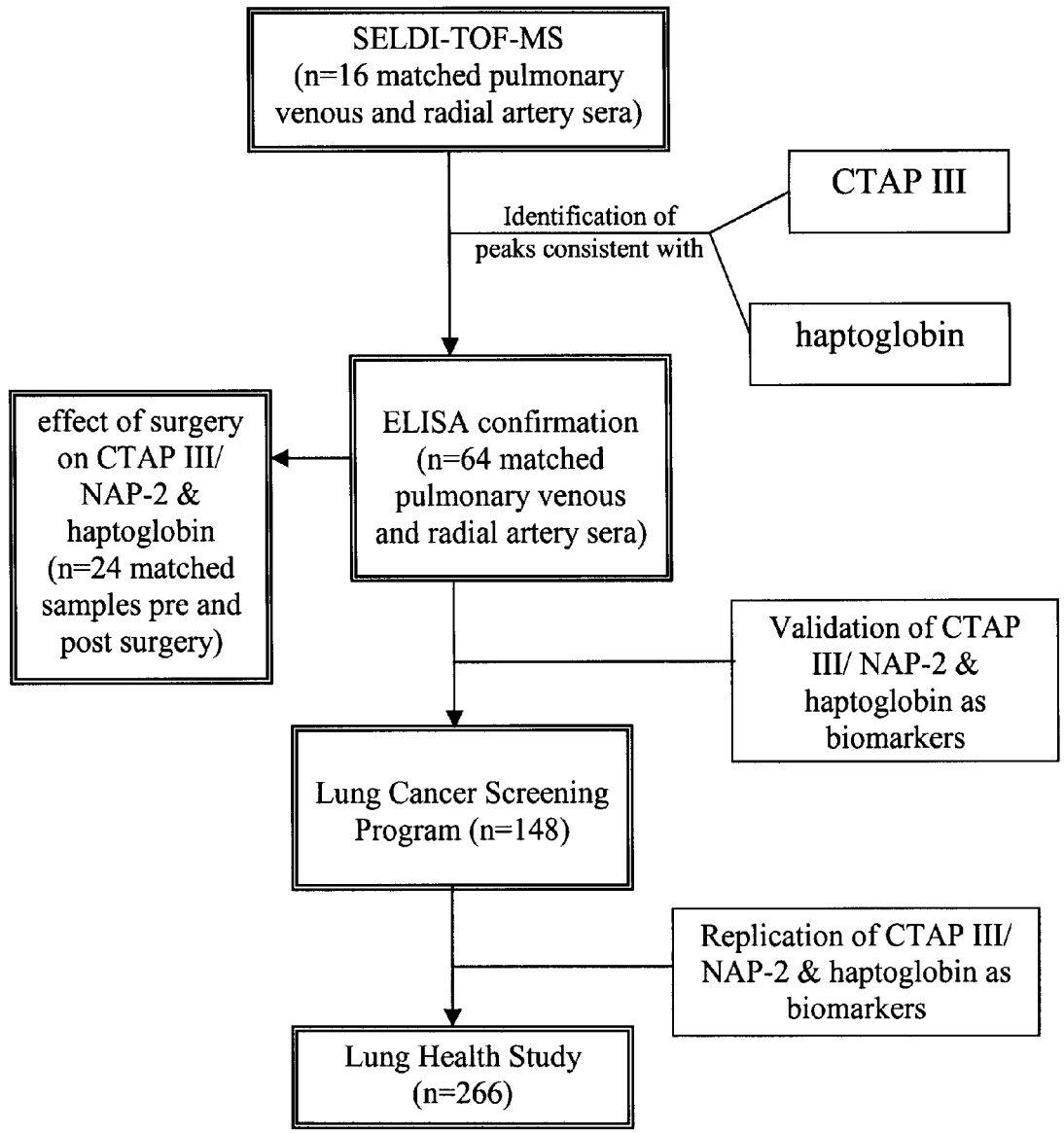
FIG. 1 outlines the study design used in the Example.

Generally, the present invention provides methods for detecting lung cancer, and for monitoring the response to lung cancer treatment.

The method for detecting lung cancer described herein comprising detecting an elevated level of a CTAP III-related biomarker in a biological sample from a subject at risk for developing lung cancer. Optionally, the method may include the additional step of detecting an increased level of haptoglobin.

The subject may be an is an individual with COPD, a smoker, or an individual with compromised lung function, or an individual having any reason for concern of being at risk for developing lung cancer.

The biological sample to be assessed in the method described herein may be blood, serum, plasma, sputum, bronchial brushings, saliva, tissue obtained through biopsy, exhaled breath, or urine.

The level of CTAP III-related biomarker detected in the method may be evaluated against a control sample obtained from the subject, or from any other appropriate control. When a subject provides his or her own control value, the biological sample comprises a subject's venous blood, plasma or serum and the control sample comprises a subject's arterial blood, plasma or serum. Optionally, the control sample may comprise a subject's previously obtained biological sample, preserved from a previous time during which the development of Jung cancer was unlikely to have been detectable.

A method of predicting risk of developing lung cancer is also described herein. This method of predicting risk comprises detecting an elevated level of a CTAP III-related biomarker in a biological sample from a subject. Detecting an increased level of haptoglobin may be an additional factor included in the assessment of risk, so that both CTAP III-related biomarker and haptoglobin are simultaneously or serially assessed. Optionally, the assessment of risk may include detecting one or more additional clinical, social, or demographic risk factors. All factors assessed may be included together in a multi-variate risk model, incorporated into a computerized analysis. The clinical, social or demographic risk factors may comprise one or more of the following factors: age, sex, smoking history, smoking status, smoking family history, education level, socio-economic status, body mass index, COPD, and/or lung function.

The assessment of risk of developing lung cancer may be carried out, for example, in a subject with COPD, a smoker, or an individual with compromised lung function. However, assessment of risk need not be limited to those individuals in a high risk group. This assessment may be of value for individuals wishing to undergo intensive health diagnostic analysis, and who may not have high risk of developing lung cancer.

The biological sample to be assessed in the method of risk assessment may be blood, serum, plasma, sputum, bronchial brushings, saliva, tissue obtained through biopsy, exhaled breath, or urine.

Levels of the CTAP III-related biomarker can be evaluated against a control sample obtained from the subject, or may be assessed against an acceptable standard from an appropriate sample and/or population. The biological sample may comprise a subject's venous blood, plasma or serum and the control sample comprises a subject's arterial blood, plasma or serum. Further, the control sample may comprises a subject's previously obtained biological sample.

According to the method of predicting risk of developing lung cancer, upon receiving an assessment based on CTAP III-related biomarker, a subject deemed to be at high risk on the basis of an elevated level of CTAP III-related biomarker may subsequently be assessed by spiral computed tomography (CT), autofluorescence bronchosocopy (AFB), or optical coherence tomography, or any other clinically acceptable follow-up strategy.

Described herein is a method of monitoring the success of lung cancer treatment with curative intent. Such a method comprises detecting levels of a CTAP III-related biomarker in a biological sample from a subject undergoing treatment for lung cancer for comparison with the a previous level obtained from the subject. The method may also comprise the step of detecting haptoglobin for comparison with a previous level obtained from the subject. In such a method, increasing levels of CTAP III-related biomarker and haptoglobin may be indicative of relapse, or indicative that not all tumor tissue was removed as a result of a surgical treatment.

Further, a kit for detecting risk of developing lung cancer is described herein. The kit comprises reagents for detecting an elevated level of a CTAP III-related biomarker in a biological sample from a subject at risk for developing lung cancer, together with instructions for use. Possible reagents include antibodies to CTAP-III-related proteins. Such a kit may also include reagents for detection of an increased level of haptoglobin, together with instructions for use.

An imaging agent, and use of an imaging agent is described herein. The agent may an antibody against CTAP III and/or CTAP III-related proteins, which may be used in diagnosis of an individual, or in determination of an increased risk of lung cancer.

Biomarkers and methods are identified herein, which are useful for the early detection of lung cancer, in assessing the risk of developing lung cancer, and in monitoring the response to treatment. These biomarkers and methods have application in early lung cancer screening tests in suitable patients and populations, for example in smokers. This invention is also useful for monitoring outcome and likelihood of recurrence after lung cancer treatment with curative intent. Such biomarkers may also be advantageously used in conjunction with determination of clinical-socio-demographic factors such as age, sex, smoking history, smoking status, smoking family history, education level, COPD, body mass index, and lung function tests in an overall lung cancer risk assessment model.

Advantageously, the use of these biomarkers permits a subject to serve as his or her own control to subtract the background noise thereby improving the signal to noise ratio. As a further advantage, biomarkers that are derived from the tumor microenvironment are evaluated, in contrast to biomarkers present as a systemic reaction to the presence of a tumor. Evaluation of blood draining from the tumor region permitted the identification of connective tissue-activating peptide III (CTAP III), a truncated form of pro-platelet basic protein (PPBP), and other proteins as biomarkers for detection of early lung cancer.

Biomarkers for early detection of lung cancer were validated using peripheral venous blood samples from two independent population-based studies from smokers not known to have lung cancer. The incremental value of evaluating these biomarkers to detect lung cancer in the context of a multi-modal lung cancer risk model that incorporates demographic, clinical factors and biomarkers was assessed.

The biomarkers described herein were discovered using the unique approach of comparing the proteomic profiles of paired pulmonary venous and radial artery blood from the same patients during surgery. Connective tissue-activating peptide III (CTAP III) and other proteins were identified to be significantly higher in venous blood versus arterial blood. This was confirmed using immunoassays against CTAP III/NAP-2. Further, CTAP III/NAP-2 levels decreased significantly following surgery (p=0.01), indicating the value of these biomarkers in detection of the presence of cancerous tissue. In two independent population cohorts, CTAP III/NAP-2 was significantly associated with lung cancer.

Advantageously, use of the biomarkers described herein as part of a multi-modal lung cancer risk model improves predictive accuracy. Including the biomarker data improved the accuracy of a lung cancer risk model that included age, smoking, lung function (FEV1) and an interaction term between FEV1 and CTAP III/NAP-2.

While chronic obstructive pulmonary disease (COPD) is associated with lung cancer, the biomarkers according to the invention can be used to improve the prediction of which patients with COPD are at increased risk of developing lung cancer.

An in vivo sample collection strategy is used to compare venous effluent blood from the tumor versus the systemic circulation. Blood samples collected from the same subject permit the subtraction of the background noise, improvement of the signal to noise ratio, and identification of biomarkers that are derived from the tumor microenvironment in contrast to a systemic reaction to the presence of a tumor. Comparison of these samples resulted in the identification of CTAP III/NAP-2 and other proteins as biomarkers for early detection of lung cancer. The biomarkers were then validated using blood samples from two independent population-based studies prior to clinical diagnosis. Validation of the biomarkers involved evaluation of venous blood from volunteer smokers with and without lung cancer prior to enrolment onto a chemoprevention trial, and smokers who participated in the NHLBI Lung Health Study.

Another aspect described herein is the application of biomarkers in conjunction with demographic and bio-measurement data (lung function). Although the biomarkers may be used as a stand-alone test for caner detection and/or risk, the interaction between lung function (FEV1%) and the biomarker CTAP III permits highly effective prediction of risk based on a plurality of risk factors. This integrated approach illustrates for the first time that an inflammatory link exists between lung cancer and chronic obstructive pulmonary disease. That COPD increases lung cancer risk has been know for a long time. An inflammatory link has been hypothesized but this is the first study that has identified a biomarker that links decline in lung function with lung cancer risk.

A lung cancer prediction model was developed using social-demographic factors and clinical data from participants in the US NCI Prostate, Lung, Colorectal and Ovarian cancer screening study. The model was validated in 2422 former and current smokers enrolled in several NCI sponsored chemoprevention trials in Vancouver. The area under the receiver operating curve (AUC) was 0.74. The incremental benefit of adding other biomarkers such as lung function or sputum atypia by image analysis was evaluated.

Addition of the biomarker parameter described herein was found to improve the AUC of the prediction model further to 0.84. The multivariate prediction model described herein provides a rapid and inexpensive screen for high risk groups, such as former and current smokers. Using this screen to identify individuals at increased risk of developing cancer permits selective screening of higher risk individuals using more intensive methods, such as spiral CT and autofluorescence bronchoscopy.

In general, biomarkers described herein include platelet basic protein (PBP), its various shortened forms such as connective tissue activating peptide (CTAP III) or NAP-2 (neutrophil activating peptide-2). Any one of these biomarkers is useful for early detection of lung cancer.

The term "CTAP III-related biomarkers" encompasses various naturally occurring polymorphisms, isoforms, shortened and truncated forms, mutants and post-translationally modified forms of the PBP, including CTAP III, and NAP-2, and its various aliases are described herein, and are encompassed by the term CTAP III-related biomarkers. CTAP III-related biomarkers encompasses related cleavage peptides that share the same amino acid sequences minus NLAK. Detailed database records and annotation for the PBP and its aliases are available in public databases, for example at:

Further data relating to PBP and the precursor PBPP can be found at: UniProtKB Entry: P02775; ENTRY NAME: SCYB7_HUMAN; ACCESSION NUMBERS: P02775; Q6IBJ8; GENE Name: PPBP; Gene Synonym: CTAP3; CXCL7; SCYB7; TGB1; THBGB1; Synonyms: PBP, C-X-C motif chemokine 7, Small-inducible cytokine B7, Leukocyte-derived growth factor, LDGF, Macrophage-derived growth factor, MDGF. Gene location: chromosome 4q12-q13.

Various shortened, processed or truncated forms of PBP protein include (as defined by "Contains" field in UniProt database entry): Connective tissue-activating peptide III (CTAP-III); Low-affinity platelet factor IV (LA-PF4); TC-2; Connective tissue-activating peptide III(1-81) (CTAP-III(1-81)); Beta-thromboglobulin (Beta-TG); Neutrophil-activating peptide 2(74) (NAP-2(74)); Neutrophil-activating peptide 2(73) (NAP-2(73)); Neutrophil-activating peptide 2 (NAP-2); TC-1; Neutrophil-activating peptide 2(1-66) (NAP-2(1-66)); Neutrophil-activating peptide 2(1-63) (NAP-2(1-63)). Each of these proteins is known and available in public databases.

Connective tissue-activating peptide III (CTAP-III), is an exemplary CTAP III-related biomarker, and is a specific truncated form of PBP that shows reliable ability among the CTAP III-related biomarkers.

The term "haptoglobin" as used herein refers to the known protein haptoglobin as well as its various aliases, some of which are noted herein. Detailed public database records/annotation for this protein are available, for example at:

Entrez Gene: 3240; UniProt: P00738; Aliases: HP, MGC111141, hp2-alpha; GenBank Accession Number: NM_005143.

The CTAP III-related biomarkers described herein are useful for monitoring outcome, and more specifically for monitoring disease recurrence after lung cancer treatment with curative intent.

Measurement of any one of the CTAP III-related biomarkers described herein, in conjunction with determination of clinical-socio-demographic factors such as age, sex, smoking, smoking history, smoking family history, education level, COPD, body mass index, and lung function tests constitutes a highly predictive lung cancer risk assessment model.

Simultaneous measurement of any of the CTAP III-related biomarkers together with haptoglobin, is useful for the early detection of lung cancer and/or for monitoring outcome (i.e. disease recurrence) after lung cancer treatment with curative intent.

Measurement of any of the CTAP III-related biomarkers together with haptoglobin can be combined with clinical socio-demographic factors such as age, sex, smoking, smoking history, smoking family history, education level, COPD, body mass index, and lung function tests to provide a lung cancer risk assessment model.

Simultaneous measurement of any of the CTAP III-related biomarkers together with both haptoglobin and MCP-1 is also useful for the early detection of lung cancer. This combination of parameters may also be used to monitor outcome (i.e. disease recurrence) after lung cancer treatment with curative intent. Further, this combination of parameters may be further assessed in a model incorporating clinical-socio-demographic factors such as age, sex, smoking, smoking history, smoking family history, education level, COPD, body mass index, and lung function tests to constitute a lung cancer risk assessment model.

Detection of increased levels of any of the CTAP III-related biomarkers can be used to indicate the presence of lung cancer and/or an elevated risk for the development of lung cancer. The assessment of increased levels of haptoglobin and/or decreased levels of MCP-1 can also be combined with assessment of CTAP III-related biomarkers to indicate the presence of lung cancer and/or elevated risk.

Levels of any of the CTAP III-related biomarkers may be assessed after lung cancer treatment with curative intent to test for disease relapse or recurrence of lung cancer. The assessment of increased levels of haptoglobin in blood and/or decreased levels of MCP-1 in the blood can also be combined with assessment of CTAP III-related biomarkers to test for disease relapse or recurrence of lung cancer.

Detection of increased levels of any of the CTAP III-related biomarkers in conjunction with clinical-socio-demographic factors such as age, sex, smoking, smoking history, smoking family history, COPD, body mass index, and lung function tests is indicative of the presence of lung cancer and/or an elevated risk for the development of lung cancer within an overall lung cancer risk assessment model. The additional parameters of levels of haptoglobin and/or levels of MCP-1 can also be combined with data in this model to provide additional sensitivity to the model.

Measurement of any of the CTAP III-related biomarkers, either as a sole parameter, or combined with measurement of haptoglobin can be useful for the early detection of lung cancer and/or and elevated risk for the development of lung cancer up to 30 months prior to clinical diagnosis of the disease.

Detection of increased levels of CTAP-III, especially in conjunction with increased levels of haptoglobin, indicates the presence of lung cancer and/or an elevated risk for the development of lung cancer. After lung cancer treatment, assessment of CTAP III either alone or in combination with haptoglobin after treatment with curative intent is indicative of disease relapse or recurrence of lung cancer. Detection up to 30 months prior to clinical diagnosis of the disease is possible.

Measurement of CTAP III-related biomarkers in individuals at risk for lung cancer such as smokers, when taken either alone or together with haptoglobin levels, in conjunction with socio-demographic factors can provide an early lung cancer risk prediction model. Parameters to be measured include, but are not limited to such factors as age, smoking status, smoking history, smoking family history, related family history, education, body mass index, recent X-ray results, presence of COPD, and bio-measurement data. Bio-measurement data may include such parameters as lung function (i.e. FEV1%), sputum atypia (assessed by image analysis etc.) or other measurements correlating to increased risk. Such a multivariate lung cancer risk prediction model can be used to rapidly and inexpensively screen former and current smokers for more intensive follow-up studies with spiral CT and/or autofluorescence bronchoscopy.

CTAP III-related biomarkers may be measured in blood, tissues or fluids other than blood, such as blood plasma, blood serum, sputum, bronchial brushings, saliva, lymphatic fluid, tissue biopsies, exhaled breath, and urine.

CTAP III-related biomarkers and methods of the invention are useful in detecting or assessing risk for all malignancies of the lung including but not limited to non-small cell lung cancer (NSCLC) and small-cell lung cancer (SCLC). The biomarkers are also useful as prognostic markers, for example to predict disease course and/or survival for lung cancer. The biomarkers are additionally useful for predicting the response to treatment of lung cancer using surgery, radiation and/or various chemotherapeutic regimens, for example, cisplatin-based agents alone or in combination with other drugs.

CTAP III-related biomarkers are useful for the risk assessment and/or early detection of other cancers, especially those of epithelial origin including but not limited to breast, prostate, skin, gastrointestinal and oral.

Detection and quantification (in blood or other tissues/bodily fluids) of protein biomarkers of the invention may be accomplished using numerous techniques, kits, reagents or procedures well known to those skilled in the art including but not limited to enzyme-linked immunosorbent assays (ELISA), radioimmunoassay (RIA), western blotting, immunohistochemistry (IHC), fluorescence and other spectroscopic based techniques and various forms of mass spectrometry (including high-throughput mass spectrometry) and aptamers.

Further aspects of the invention will become apparent from consideration of the ensuing description of preferred embodiments of the invention. A person skilled in the art will realize that other embodiments of the invention are possible and that the details of the invention can be modified in a number of respects, all without departing from the inventive concept. Thus, the following drawings, descriptions and examples are to be regarded as illustrative in nature and not restrictive.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

EXAMPLE

Determination of CTAP III-Related Biomarkers

Methods

FIG. 1 outlines the study design. At the time of thoracotomy and resection of the tumor, two blood samples were obtained: 1) from the lobar pulmonary vein that received drainage directly from the tumor containing lung segment that should contain the highest concentration of a candidate biomarker; and 2) from the radial artery which represents the systemic circulation. Serum samples from pulmonary venous and systemic blood were fractionated and analyzed using surface-enhanced laser desorption ionization time-of-flight mass spectroscopy (SELDI-TOF-MS). Levels of two proteins were significantly increased in pulmonary venous compared to systemic blood from the radial artery. These proteins were identified as Connective Tissue-Activating Peptide III (CTAP III) and haptoglobin using tandem MS (MS/MS). Enzyme-linked immunosorbent assay (ELISA) was used to validate that the proteins identified were differentially expressed between pulmonary venous and systemic blood and that their levels changed following surgical removal of the lung tumor. Finally, their concentrations in peripheral venous blood were compared between heavy smokers who did and did not develop lung cancer using blood samples from two independent cohorts: 1) a lung cancer prevention study at the BC Cancer Agency; and 2) the NHLBI Lung Health Study (LHS)[17]. The incremental value of these biomarkers to demographic and clinical factors was evaluated for detection of pre-clinical lung cancer.

As illustrated in FIG. 1, the study design involved the following steps noted below. 1) Proteomic profiling using SELDI-TOF MS was used on matched sera from pulmonary vein draining the tumor and systemic blood from 16 subjects at the time of surgery. Identification of differential peaks consistent with CTAP III/NAP-2 and haptoglobin (HP) by tandem mass spectrometry (MS/MS) using the QSTAR™ MS (ABI) led to the discovery of CTAP III as a novel biomarker for detection of lung cancer. 2) Differential expression was confirmed in 64 matched sera from pulmonary vein and radial artery of surgical patients using ELISA against CTAP III/NAP-2. 3) CTAP III/NAP-2 and haptoglobin was measured from peripheral venous blood before and after surgery in 28 patients with early lung cancer 5 of whom were later found to have recurrent lung cancer on follow-up to determine if these biomarkers can detect microscopic residual disease after surgical resection. 4) CTAP III/NAP-2 and haptoglobin as potential lung cancer detection biomarkers were validated using peripheral venous blood from smokers participating in a Lung Cancer Prevention Study at BCCA (n=149). 5) The findings from the Lung Cancer Prevention Study were replicated in the NHLBI Lung Health Study using a nested case-control design (n=266).

Study Participants. The patients in the first and second parts of the study were surgical patients at the Vancouver General Hospital (Vancouver, Canada).

Table 1 provides the demographics, histological cell type and stage of lung cancer of the 16 patients in the first part (i.e. discovery phase) and the 64 patients in the second part of the study (i.e. confirmatory phase using ELISA).

TABLE 1

Demographic and Clinical Data in Surgical Patients

| | SELDI-MS/MS Study | Venous-Arterial ELISA Study | Pre- & Post Surgery ELISA Study |
|---|---|---|---|
| Total number | 16 | 64 | 28 |
| Age (years), mean (SD) | 69 ± 6 | 69 ± 9 | 61 ± 9 |
| Age, range (years) | 58-76 | 44-85 | 48-75 |
| Men:Women | 10:8 | 30:34 | 13:15 |

TABLE 1-continued

Demographic and Clinical Data in Surgical Patients

| | SELDI-MS/MS Study | Venous-Arterial ELISA Study | Pre- & Post Surgery ELISA Study |
|---|---|---|---|
| Current/former/never smokers | 9/6/3 | 11/53/0 | 13/15/0 |
| Smoking (pack-years) | 47 ± 17 | 47 ± 21 | 52 ± 22 |
| $FEV_1$ % of Predicted | 71 ± 15 | 71 ± 16 | 79 ± 20 |
| Squamous cell carcinoma n (%) | 1 (16%) | 20 (31%) | 11 (39%) |
| Adenocarcinoma, n (%) | 12 (67%) | 36 (56%) | 15 (53%) |
| Small cell carcinoma, n (%) | 3 (16%) | 1 (2%) | 1 (4%) |
| Other, n (%) | 2 (11%) | 7 (11%) | 1 (4%) |
| Stages, n (%) | | | |
| 0 | 0 | 0 | 6 (21%) |
| IA | 1 (6%) | 20 (31%) | 16 (57%) |
| IB | 8 (44%) | 24 (38%) | 0 |
| II | 7 (38%) | 14 (22%) | 2 (7%) |
| III | 1 (6%) | 5 (7%) | 3 (11%) |
| IV | 1 (6%) | 1 (2%) | 1 (4%) |

Abbreviations: ELISA, enzyme-lined immunosorbent assay; $FEV_1$, forced expiratory volume in one second; SELDI, surface-enhanced laser desorption ionization.

The participants in the third and fourth parts of the study were from two separate population-based cohorts. The first cohort comprised of asymptomatic smokers between 45 to 74 years of age with a smoking history of ≥30 pack years. Subjects were excluded from the study if they had a history of prior malignancy except non-melanomatous skin cancer, localized prostate cancer, carcinoma in situ of cervix, or superficial bladder cancer without evidence of recurrence after treatment for 5 or more years. They were screened with autofluorescence bronchoscopy and/or spiral CT prior to enrollment into one of several NCI sponsored lung cancer chemoprevention trials (NIH-NCI contract N01-CN-85188 and NCI grant 1PO1-CA96964, U01CA96109). Blood samples from 49 participants found to have lung cancer and 100 smokers without lung cancer randomly selected from the cohort were used for the biomarker validation study. At the time of the peripheral venous blood collection, none of the study participants had a clinical diagnosis of lung cancer. Lung cancer was subsequently diagnosed in 49 participants. The median interval from blood collection to the diagnosis of lung cancer was 6 months (interquartile range, 2 to 29 months).

Table 2 shows the characteristics of twenty-four of the 49 participants with lung cancer, who also had blood samples available following surgical resection of their tumor. As controls, blood samples from 100 smokers without lung cancer from the same screening cohorts were randomly selected and used for the biomarker validation study. Twenty-eight of the 49 participants with lung cancer also had blood samples available following surgical resection of their tumor. Archival blood samples from a second population based cohort (LHS)[17,18] were also used for validation of the biomarkers and for determining the incremental value of these biomarkers to demographic and clinical factors. The LHS blood samples were collected between 1992 to 1994. We performed a case-control study wherein we identified 45 smokers who died of lung cancer within 5 years of their blood sampling and 221 control smokers without lung cancer who were matched for age, gender, race, smoking status (which was validated by salivary cotinine levels), body mass index (BMI) and lung function (forced expiratory volume in one second [$FEV_1$] as percent of predicted). We matched at least 5 controls for every case[19]. The median interval from blood collection to lung cancer death in this cohort was 39 months (interquartile range, 26 to 49 months). We matched at least 5 controls for every case[19]. Informed consent was obtained from the participants. The study was approved by the research ethics board of the University of British Columbia.

TABLE 2

Demographic & Clinical Data of Lung Cancer Chemoprevention Study Participants

|  | Control Participants | Participants With Lung Cancer |
|---|---|---|
| Total number | 100 | 49 |
| Age (years), mean (SD) | 61 ± 6 | 63 ± 9 |
| Age, range (years) | 50-73 | 48-80 |
| Men:Women | 50:50 | 30:19 |
| Current/former smokers | 16/84 | 26/23 |
| Smoking (pack-years) | 48 ± 19 | 55 ± 27 |
| Duration of smoking cessation (years), mean (SD) | 9 ± 7 | 9 ± 8 |
| $FEV_1$ % of predicted | 91 ± 16 | 76 ± 24 |
| Squamous cell carcinoma n (%) | — | 15 (31%) |
| Adenocarcinoma, n (%) | — | 19 (40%) |
| Small cell carcinoma, n (%) | — | 8 (17%) |
| Other, n (%) | — | 7 (12%) |
| Stages, n (%) |  |  |
| 0 | — | 7 (14%) |
| IA | — | 16 (33%) |
| IB | — | 3 (6%) |
| II | — | 4 (8%) |
| III | — | 8 (17%) |
| IV | — | 11 (22%) |
| Interval between blood sampling & lung cancer diagnosis (months) | — | 6 (2 to 29) median (Interquartile range) |

Abbreviations: $FEV_1$, forced expiratory volume in one second

Table 3 shows the clinical characteristics of subjects who died from lung cancer and matched controls from the NHLBI Lung Health Study. The median interval from blood collection to lung cancer death in this cohort was 39 months (interquartile range, 26 to 49 months). We matched up to 5 controls for every case[31]. The study was approved by the research ethics board of the University of British Columbia.

TABLE 3

Clinical Characteristics Of Subjects Who Died From Lung Cancer and Matched Controls from the NHLBI Lung Health Study

|  | Control Subjects | Lung Cancer Subjects | P-value |
|---|---|---|---|
| Total number | 221 | 45 |  |
| Age (years) | 59 ± 4 | 59 ± 4 | 0.86 |
| Age range | 49-64 | 50-65 | — |
| Smoking (pack-years) | 46 ± 21 | 47 ± 18 | 0.88 |
| BMI (kg/m$^2$) | 25.0 ± 3.43 | 24.8 ± 3.8 | 0.72 |
| Men:Women | 120:101 | 24:21 | 0.91 |
| $FEV_1$ (liters) | 2.27 ± 0.60 | 2.21 ± 0.65 | 0.60 |
| $FEV_1$ (% Predicted) | 72.16 ± 10.93 | 70.83 ± 13.39 | 0.53 |
| CRP (log-scale; ng/ml) | 15.10 ± 1.33 | 15.06 ± 1.28 | 0.86 |
| Sustained Quitters* | 20 (9%) | 4 (9%) | 0.99 |
| Intermittent Quitters | 70 (32%) | 14 (31%) |  |
| Continuous Smokers | 131 (59%) | 27 (60%) |  |

Continuous variables are shown as mean ± SD and categorical variables are shown as number (% column totals)
*sustained quitters were defined as individuals who quit smoking during the 5 years of follow-up verified by salivary cotinine levels. Continuous smokers were individuals who continued to smoke during follow-up and intermittent quitters were those who quit and then restarted smoking during follow-up.
Abbreviations: BMI, body mass index; CRP, C-reactive protein; FEV1, forced expiratory volume in one second Blood Collection and Processing. In the surgical patients, blood (10 ml) was collected simultaneously from both the pulmonary vein (draining the tumor-containing segment) and radial artery in a serum separator tube, clotted for 30 minutes, centrifuged, aliquoted and flash frozen at −80° C. The paired sera were fractionated by pI and analyzed by SELDI-TOF-MS or by ELISA. In the lung cancer screening study and LHS participants, blood from a peripheral vein were collected into $K_2$EDTA tubes and centrifuged immediately at 4° C. The resultant supernatant plasma was transferred into two cryotubes until assay. All blood samples were processed and stored at −80° C. within 2 hours after blood draw.

Serum Fractionation for SELDI-TOF-MS Analysis. Aliquots of serum sample were centrifuged (10min at 4° C., 20,000×g) to remove insoluble material. Samples (20 μl) were denatured for 1 hr at 4° C. with 30 μl of U9buffer (9M Urea, 2% 3-[(3-Cholamidopropyl)dimethylammonio]-1-propanesulfonate (CHAPS), 50 mM Tris-HCI pH 9). Anion exchange chromatography was performed in parallel using a PROTEINCHIP™ Serum Fractionation kit with a 96-well filter plate containing desiccated anion exchange resin as per the manufacturer's instructions (Bio-Rad Laboratories, Hercules, Calif.). Following rehydration, washing and equilibration of the anion exchange resin, denatured serum samples were applied and allowed to bind for 30 min at 4° C. with shaking. Six fractions were collected from each sample. We used Fraction 1 containing the unbound protein flow-through pooled with a pH 9 elution.

SELDI-TOF-MS Analysis. Weak cation exchange PROTEINCHIP™ arrays were used to bind the proteins in Fraction 1 using a bioprocessor reservoir as per manufacturer's instructions (CM10 PROTEINCHIP™ Array Kit, Bio-Rad Laboratories). The limit of detection of the PROTEINCHIP™ surfaces has been determined to typically be in the low femtomole range with a linear response over 2-3 orders of magnitude[38,39]. The average percent coefficient of variation (%CV) observed for peaks across the 2,500-150,000 m/z range have been shown to be better than 25% and peaks in the 10,000-15,000 m/z range exhibited less variation with an average %CV of 20%[40]. Ten μl of Fraction 1 samples was added to 90 μl of low stringency CM10 binding buffer (0.1 M sodium acetate, pH 4.0) to washed and equilibrated CM10 arrays. Binding was conducted with vigorous shaking for 1 hr, followed by 3 washes with binding buffer and a final water wash. PROTEINCHIP™ arrays were air dried prior to the addition of sinapinic acid (SPA) matrix (12.5 mg/ml SPA, 50% v/v ACN, 0.5% v/v TFA). Prepared PROTEINCHIP™ arrays were analyzed using a SELDI-TOF MS (PBSII, Ciphergen Biosystems, Fremont, Calif.) externally calibrated using an All-in-One Protein Standard (Ciphergen Biosystems, Inc.). Spectra were generated using an average of 100 laser shots using laser intensities of 225 or 250. The resulting spectra were externally calibrated, baseline subtracted, and normalized to total ion chromatogram (TIC) using Ciphergen Express software (Ciphergen Biosystems, Inc.). Peaks were auto-detected between a mass range of 2,000-200,000 m/z. First pass criteria requiring a signal to noise ratio (S/N)>5.0 was used to identify well defined peaks. A second less stringent pass was employed to define lower intensity peaks (S/N>2.5) differing between groups. Processed spectra were analyzed using Ciphergen Express data analysis software. Normalized peaks from the pulmonary veins (test, positive group for ROC analysis) were compared to those detected in the systemic blood (radial artery).

Figure 2:
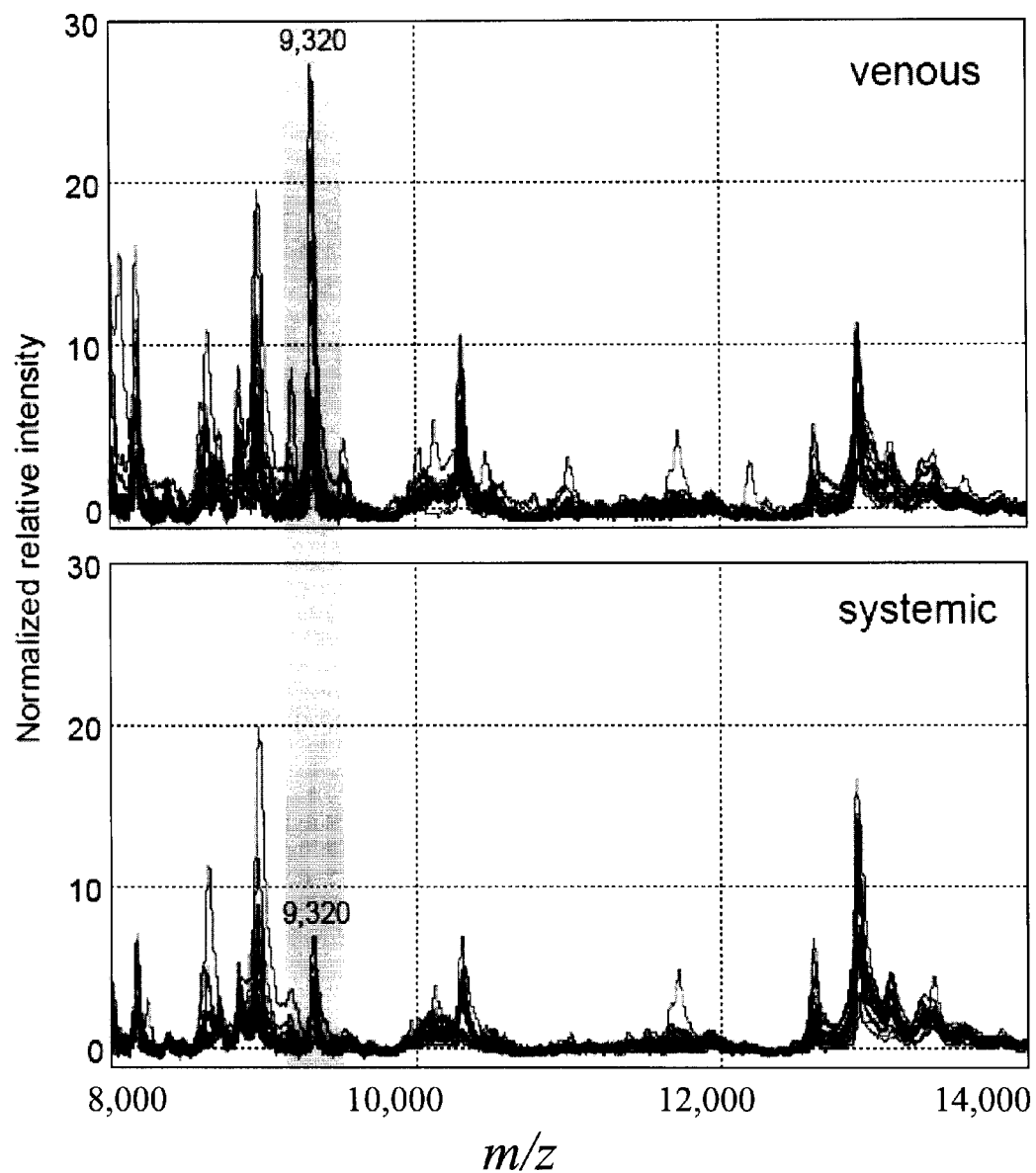
FIG. 2 illustrates a protein of interest at 9320 Da
Figure 3:
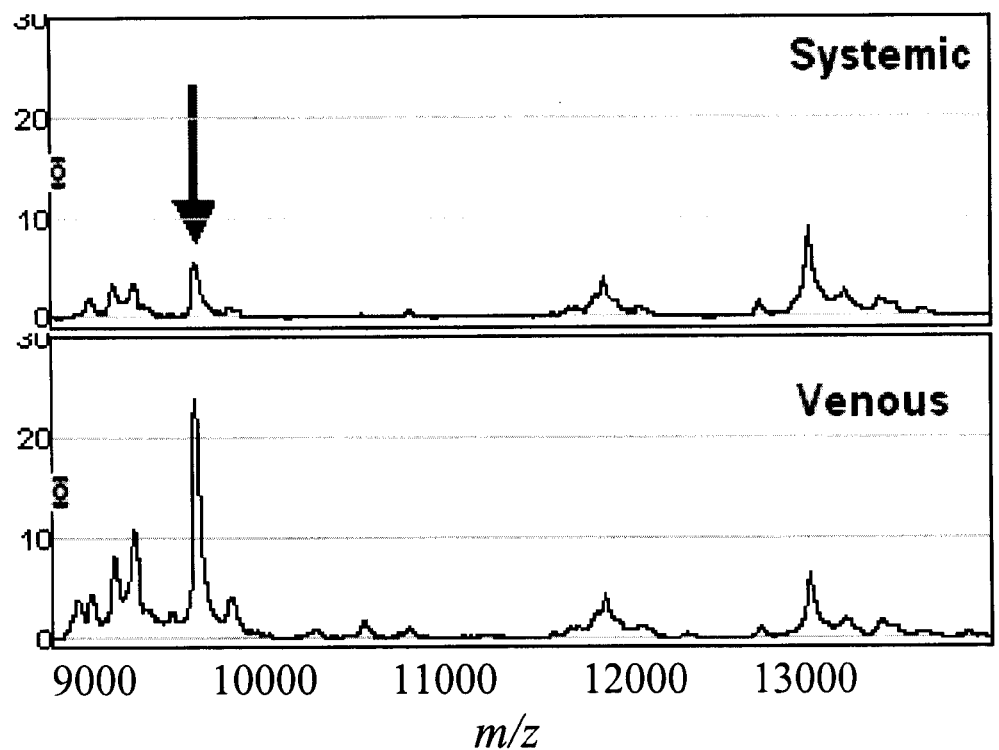
FIG. 3 shows that the peak 33 in Fraction 1 (9320 Da) increased in venous blood sample (p-value 0.002267; ROC 0.7968)
Figure 4:
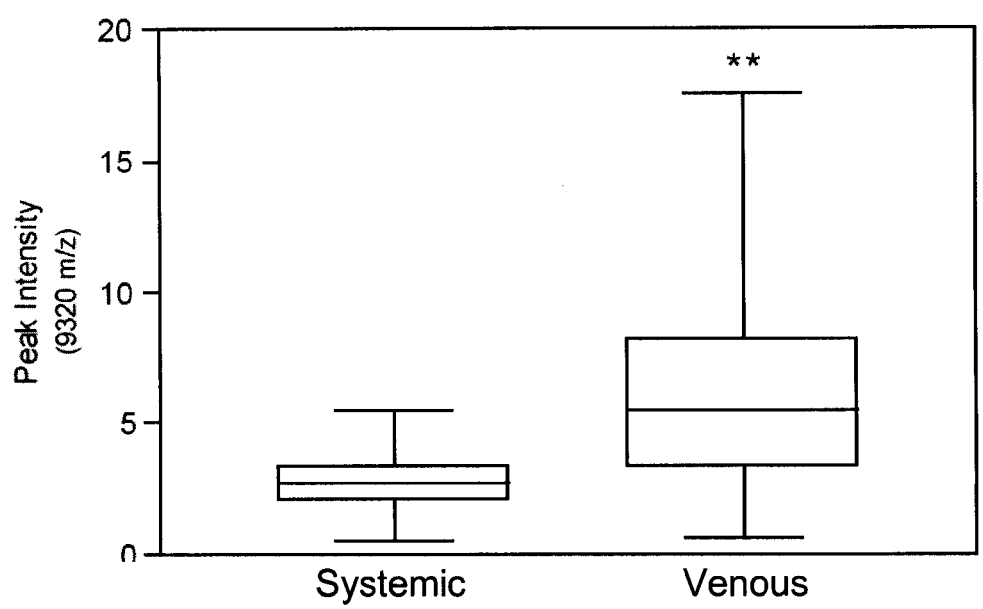
FIG. 4 illustrates systemic versus venous peak intensity for the protein at 9320 Da, specifically an increase in venous blood.

Identification of proteins that were increased in samples from the pulmonary lobar vein draining the tumor compared to systemic blood. SELDI-TOF-MS profiles from 16 paired venous-arterial sera were compared. We focused on one peak at approximately 9,320 m/z that was significantly elevated in Fraction 1 in pulmonary venous samples compared with systemic samples (FIG. 2). The total ion chromatograms of the spectra were normalized and the scales kept consistent to allow comparison of the differences in the level of intensity for 9,320 m/z. The spectra were overlaid to aid in the visualization of the pronounced differences in levels of this peak between the two sources of blood. Enhanced analysis of this region of the spectra is shown for 9,320 m/z for matched samples from the patient with the highest peak intensity of all samples (FIG. 3). This patient had a Stage II non-small lung cancer. There was no feature in this patient that could distinguish him from the remaining 15 in terms of cell type or tumor stage. Statistical analysis of peak intensities of the spectra revealed the differences observed at 9,320 m/z in venous serum samples of patients were significantly increased compared to the arterial samples (p=0.0023) (FIG. 4).

Protein isolation. To identify the protein at 9320 m/z, aliquots of serum sample (2×100 µl) were denatured with U9 buffer (150µl each) and bound to Q Ceramic HyperD F anion exchange resin (Pall, New York, N.Y.), Samples were fractionated using pH based elutions as described above. Efficiency of protein enrichment in each fraction was monitored by SELDI-TOF-MS analysis using PROTEINCHIP™ chemistries and binding protocols already described. SELDI analysis was used to identify the fraction containing the highest intensity signal at 9320 m/z for subsequent fractionation using reversed phased C18 resin (RPC PolyBio C18 resin, BioSepra, Cergy, France). Fractions were acidified with TFA (0.1% v/v TFA final concentration) and allowed to batch bind C18 resin for 30 min at 4° C. in spin columns with end over end rotation. Unbound sample flow through was collected and the sample was fractionated in a stepwise manner using 10% increases in acetonitrile concentration (0-100% ACN) with 0.1% v/v TFA. The serum fraction containing sufficiently enriched 9320 m/z peak was evaporated to dryness followed by rehydration in 4×LDS reducing sample buffer (20 µl) and analysed by Bis-Tris (12% or 4-10% polyacrylamide) SDS-PAGE with MES SDS running buffer (Invitrogen, Carlsbad, Calif.). Protein bands were visualized using a colloidal coomassie G-250 stain (Colloidal Blue Staining Kit, Invitrogen). Selected SDS-PAGE bands were excised and trypsin digested. Trypsin digests (1 µl) were spotted onto normal phase SELDI arrays (NP20, Bio-Rad Laboratories), dried, washed with water (3×10 µl), air dried, and 1 µl of a saturated α-cyano-4-hydroxycinnamic acid solution (50% v/v ACN, 0.5% TFA) was added as matrix. Samples were analysed using a quadrupole time-of-flight MS (QSTAR™ XL, Applied Biosystems/MDS Sciex, Foster City, Calif.) equipped with a SELDI ionization source (PCI-1000, Ciphergen) running Analyst QS 1.1. Survey scans (1,000-2,500 m/z) were acquired for the purpose of selecting ions for MS/MS analysis. The most intense ions observed by TOF-MS were selected for MS/MS analysis. Product ion MS/MS spectra were acquired by accumulating 100-300 scans for each selected peptide using collision induced dissociation (CID). All product ion MS/MS spectra were acquired using a mass range from 100 m/z to an upper range that included the precursor mass selected for MS/MS fragmentation. All spectra were acquired in positive ion mode, and the mass spectrometer was externally mass calibrated using MS/MS fragment ions of human [Glu$^1$-fibrinopeptide B (Sigma-Aldrich, St. Louis, Mo.).

MS/MS data analysis. QSTAR™ IDA files were viewed using Analyst QS 1.1 software. A built in Mascot script (1.6b21 ABI-Matrix Science Limited) was used to create the peak lists from all files. QSTAR™ data charge states were calculated from the TOF-MS scan and ions with a charge state of +1 used. Spectra were discarded if they contained less than 10 peaks. MS/MS data were centroided but not de-isotoped. These peak lists were then sent to a local Mascot search engine V 2.2(Matrix Science Limited). Trypsin was selected as the digest enzyme and up to 1 missed cleavage was allowed. Searches of trypsin digests with no reduction and alkylation were performed using propionamide modification of Cys, oxidation of Met, and deamidation of Asn/Gln were used as variable modifications. Searches of all other trypsin digests were performed using carbamidomethyl modification of Cys as a fixed modification with oxidation of Met, and deamidation of Asn/Gln used as variable modifications. Additional parameters used for the search of QSTAR™ data include a peptide tolerance of ±0.5 Da and MS/MS tolerance of ±0.3 Da of the monoisoptopic mass and MALDI-QUAD-TOF selected for the instrument. The sequence database searched was the International Human Protein Index (IPI_human, release 3.36 , EMBL-EBI) which provides a minimally redundant yet maximally complete set of proteins for humans (one sequence per transcript) containing 69,012 entries.

Figure 7:
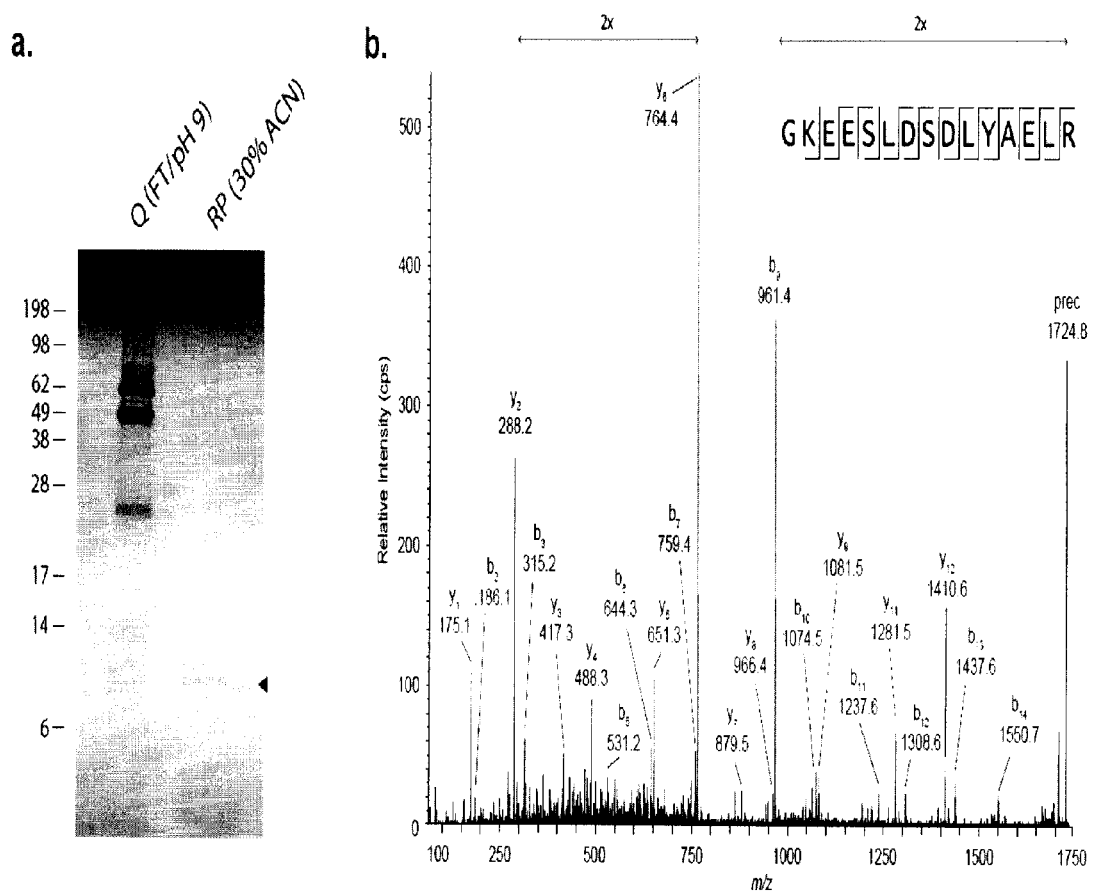
FIG. 7 shows the isolation and identification of the protein at 9320 m/z using a preparative 1D gel followed by MS/MS.

Identification of the 9,320 mlz protein. The serum sample chosen for enrichment and identification of the 9,320 m/z peak was from the patient with the highest peak intensity in the venous sample. Anion exchange Fraction 1 was prepared from 200 µl of serum and subjected to hydrophobic fractionation using reversed phase resin. The maximum signal intensity of the 9,320 m/z peak was observed by SELDI-TOF-MS analysis, using an NP20 PROTEINCHIP™ array, in the 40% ACN, 0.1% TFA fraction. Following vacuum concentration to dryness, the reconstituted sample was analyzed by SDS-PAGE (FIG. 7, part a) and a colloidal Coomassie stained band was observed with a relative mobility ($M_r$) of approximately 9 kDa. The intact mass of this band was confirmed to be the 9,320 m/z peak by passively eluting the protein from a portion of the band and confirming its mass by SELDI-TOF-MS analysis on a PBSIIc using an NP 20 PROTEINCHIP™ array. The remainder of the protein band, plus a blank region at the edge of the gel were excised and subjected to in gel trypsin digestion and tandem MS/MS analysis using a QSTAR™ XL equipped with SELDI ionization source. A Mascot MS/MS query of all 4 MS/MS spectra from the top four most intense ions (1724.8,1583.8, 1198.6, and 1070.5[M+H]$^+$) was performed against the IPI Human database with a significance threshold of p<0.01. All 4 MS/MS spectra were assigned to four peptides contained in the C-terminal portion of the mature chain of pro- platelet basic protein (PPBP)(Uniprot P 02775). Taking into consideration the observed 9320 m/z which corresponded to CTAP III, the 85 amino acids truncation of PPBP, there was 46% sequence coverage. (FIG. 7, part b). Further confirmation of protein identification was provided by manual validation of all MS/MS peptide assignments.

Haptoglobin/HPT/P00738 (20,996 m/z) was also identified by LC-MS/MS in a trypsin digest of a 20 kDa $M_r$ band from Fraction 1 of a patient's venous sample who had the highest intensity by similar methods (data not shown).

No other proteins besides CTAP III and haptoglobin were identified. Although other peaks (6 more in fraction 1, 3 peaks in fraction 4, and 4 peaks in fraction 6) were significantly (p<0.02) altered between systemic and venous blood in all of the fractions examined, we pursued identification of only the two presented here. Many of the peaks (8 peaks) were at an m/z that were very small <3000-4000 Da which are difficult to isolate by standard gel approaches. Proteins that have very small differences between pulmonary venous and arterial blood are also unlikely to pan out when measured in peripheral venous blood since the proteins will be diluted in several liters of blood. Thus, we first wanted to ensure the validity of our approach as shown here with these two extremely promising proteins. CTAP III (m/z 9320): mean systemic intensity=2.617+/−0.3315, mean venous intensity=6.607+/−1.165, n=16, p=0.0023, ROC 0.797. Mean fold increase (comparing individual patients): 2.91+/−1.85.

Measurement of Proteins Using Enzyme-Linked Immunosorbent Assay (ELISA). Levels of CTAP III in plasma samples were measured using an ELISA kit against human CTAP III/NAP-2, the c-terminal 70 amino acid region which is present in all pro-platelet basic protein species (DuoSet, R&D Systems, Minneapolis, Minn.). Haptoglobin that was found to be differentially expressed in part one of this study and proteins that have been cited in the literature as promising biomarkers for lung cancer such as C-reactive protein (CRP), serum amyloid A (SAA), and alpha-1 antitrypsin were also measured using ELISA kits in accordance with the manufacturer's instructions.[11-13,20-24].

The anti-NAP-2 antibody was obtained from DuoSet, R&D Systems, Minneapolis, Minn. It was produced in goats immunized with purified, *E. coli*-derived, recombinant human neutrophil activating peptide 2 (rhNAP-2)[34]. NAP-2 specific IgG was purified by human NAP-2 affinity chromatography. It is anticipated that this antibody will also detect the precursor proteins such as CTAP III, beta-thromboglobulin (β-TG) and platelet basic protein (PBP) that shared the same the c-terminal 70 amino acid region[34,41,42]. To make a more specific antibody for CTAP III, which only has 4 amino acids more than b-thromboglobulin, would also detect PBP thereby eliminating the possibility of a specific antibody for CTAP III. However, there was no cross-reactivity or interference with the assay by ENA-70, ENA-74, ENA-78, GCP-2, GRO-α, GRO-β, GRO-γ, IL-8, IP-10, MIG, SDF-α, SDF-β. Consistent with the MS data for detection of a species that was 9320 Da with coverage for CTAP III, the fold-difference for the ELISA data was similar to the fold difference in peak intensity from MS (e.g. approximately 3-fold difference). The lower limits of detection were: 0.015 ng/ml for CTAP III/NAP-2. The mean CV of the NAP-2 measurements was 3.9%. To validate whether the sample values reported were accurate, we performed several spike/recovery experiments on the plasma samples. The mean recovery rate was 107%, which is considered to be in the good to excellent range. The lower limit of detection for the other proteins were 0.010 ng/ml for CRP (R and D Systems, Minneapolis, Minn.); 3.13 ng/ml for haptoglobin (Immunology Consultants Laboratory, Newberg, Oreg.); 4 ng/ml for SAA (BioSource International, Camarillo, Calif.); and 7.8 ug/ml for alpha-1 antitrypsin (Immunology Consultants Laboratories, Newberg, Oreg.).

Statistical Analysis. A Wilcoxon signed rank test was used to compare protein levels between the pulmonary venous and systemic blood in the same patient undergoing surgery for lung cancer and the protein levels before and after surgery. A Wilcoxon rank sum test compared protein levels between subjects who did and did not develop lung cancer in the Lung Cancer Prevention Study. Multiple logistic regression modeling was employed to describe the relationship between levels of proteins and the risk of lung cancer, adjusted for age, gender, smoking status, and $FEV_1\%$ predicted. A stepwise model selection process was used to arrive at a parsimonious model. Receiver operating characteristic (ROC) curves were plotted to evaluate the sensitivity and specificity of the biomarker measurements in predicting lung cancer. For the analysis of the matched nested case control samples from LHS, we used conditional logistic regression to model the instantaneous rates of lung cancer mortality[25]. A two-tailed P value <0.05 was considered significant. All analyses were conducted using SAS version 9.1 (Carey, N.C.) and R 2.5.1. Continuous variables are expressed as mean ± SD unless otherwise indicated.

Identification of Differential Serum Protein Levels Between Pulmonary Lobar Vein Draining from the Tumour Versus Systemic Blood. The average age of the patients for this component of the study was 69±9 years; 47% were men; and 17% were current smokers with a FEV1 of 71±15% of predicted (refer to Table 1 ). Systemic and venous pairs of serum from 16 patients were fractionated by µl and analyzed SELDI-TOF-MS using a CM10 chip. The limit of detection of the PROTEINCHIP™ surfaces has been determined to typically be in the low femtomole range with a linear response over 2 -3 orders of magnitude[17,18]. The average percent coefficient of variation (%CV) observed for peaks across the 2,500-150,000 m/z range have been shown to be better than 25% and peaks in the 10,000-15,000 m/z range exhibited less variation with an average %CV of 20%[19]. The resulting protein profiles were compared and 8 peaks in Fraction 1 were identified as being significantly elevated in pulmonary venous samples.

FIG. 2 shows a protein fraction of interest in venous versus systemic blood. Overlay trace view of SELDI-TOF MS spectra obtained using venous (top) and systemic (bottom) serum samples from 16 lung cancer patients with a CM 10 PROTEINCHIP™ Array between 8000 and 14000 m/z. The grey box highlights the enhanced intensity at 9320 m/z that predominates in the venous group of samples compared to the systemic samples. SELDI spectra were normalized using total ion current normalization (TIC) in this and all subsequent SELDI-TOF MS spectra presented. Instrument settings were optimized to prevent saturation during spectra collection. The matrix noise region (<1000 m/z with SPA) saturates and was omitted from analyses (including TIC normalization). We focused on one peak at approximately 9,320 m/z that was predominantly increased in pulmonary venous compared with systemic samples from 16 lung cancer patients. The total ion chromatograms of the spectra have been normalized and the scales kept consistent to allow comparison of the differences in the level of intensity for 9,320 m/z measured for venous and systemic samples. The spectra were overlaid to aid in the visualization of the pronounced differences in levels of this peak between the two sources of blood.

FIG. 3 illustrates an enhanced analysis of this region of the spectra shown for 9,320 m/z for matched samples from the patient with the highest spectral intensity. Comparison is made of the intensity of the 9320 m/z region between systemic and venous matched samples from one patient to highlight the differences in the intensity of this peak. The arrow points to 9320 m/z. This patient had a Stage II non-small lung cancer. There was no feature in this patient that could distinguish him from the remaining 15 in terms of cell type or tumor stage.

FIG. 4 is a box and whisker plot of peak intensities for the 9320 m/z peak. Biological replicates with the average intensity of the 9320 m/z peak in systemic or venous serum samples from patients with lung cancer that was found to be significantly increased in venous samples. Mean systemic intensity=2.617+/−0.3315, mean venous intensity=6.607+/−1.165, n=16, (p-value 0.002267; ROC 0.7968). Mean fold increase (comparing individual patients): 2.91+/−1.85. These data illustrate statistical analysis of peak intensities of the spectra revealed the differences observed at 9,320 m/z in venous serum samples of patients were significantly increased compared to the arterial samples (n=16, p=0.0023).

Table 4 shows the relationship between biomarkers, clinical characteristics and the risk of lung cancer in the BCCA Lung Cancer Prevention Study.

TABLE 4

Relationship Between Biomarkers, Clinical Characteristics and the Risk of Lung Cancer in the BCCA Lung Cancer Prevention Study

| Variable | β-coefficient ± standard error* | P-value |
|---|---|---|
| Haptoglobin (ug/ml) | 1.07 ± 0.50 | 0.031 |
| CTAP III/NAP-2 (ng/ml) | 2.95 ± 1.15 | 0.010 |
| Age (year) | 0.05 ± 0.03 | 0.108 |
| FEV$_1$ % predicted | 0.20 ± 0.09 | 0.026 |
| Current Smokers (versus ex-smokers) | 1.08 ± 0.25 | <0.001 |
| CTAP III/NAP-2 × FEV$_1$ % Predicted (Interaction term) | −0.03 ± 0.01 | 0.009 |

A logistic regression model was used to estimate the odds of lung cancer, adjusted for all of the variables listed in the table.
*for every one unit increase As illustrated in FIG. 2, relating to SELDI-TOF MS Analysis, an overlay trace view of SELDI-TOF MS spectra obtained using venous and systemic serum samples from 16 lung cancer patients with a CM 10 PROTEINCHIP™ Array between 8000 and 14000 m/z. The grey box highlights the enhanced intensity at 9320 m/z that predominates in the venous group of samples compared to the systemic samples. SELDI spectra were normalized using total ion current normalization (TIC) in this and all subsequent SELDI-TOF MS spectra presented. Instrument settings were optimized to prevent saturation during spectra collection. The matrix noise region (<1000 m/z with SPA) saturates and was omitted from analyses (including TIC normalization).

FIG. 3 shows a comparison of the intensity of the 9320 m/z region between systemic and venous matched samples from one patient to highlight the differences in the intensity of this peak. The arrow points to 9320 m/z.

FIG. 4 shows a box and whisker plot of peak intensities for the 9320 m/z peak. Biological replicates with the average intensity of the 9320 m/z peak in systemic or venous serum samples from patients with lung cancer that was found to be significantly increased in venous samples (p-value 0.002267; ROC 0.7968).

Figure 5:
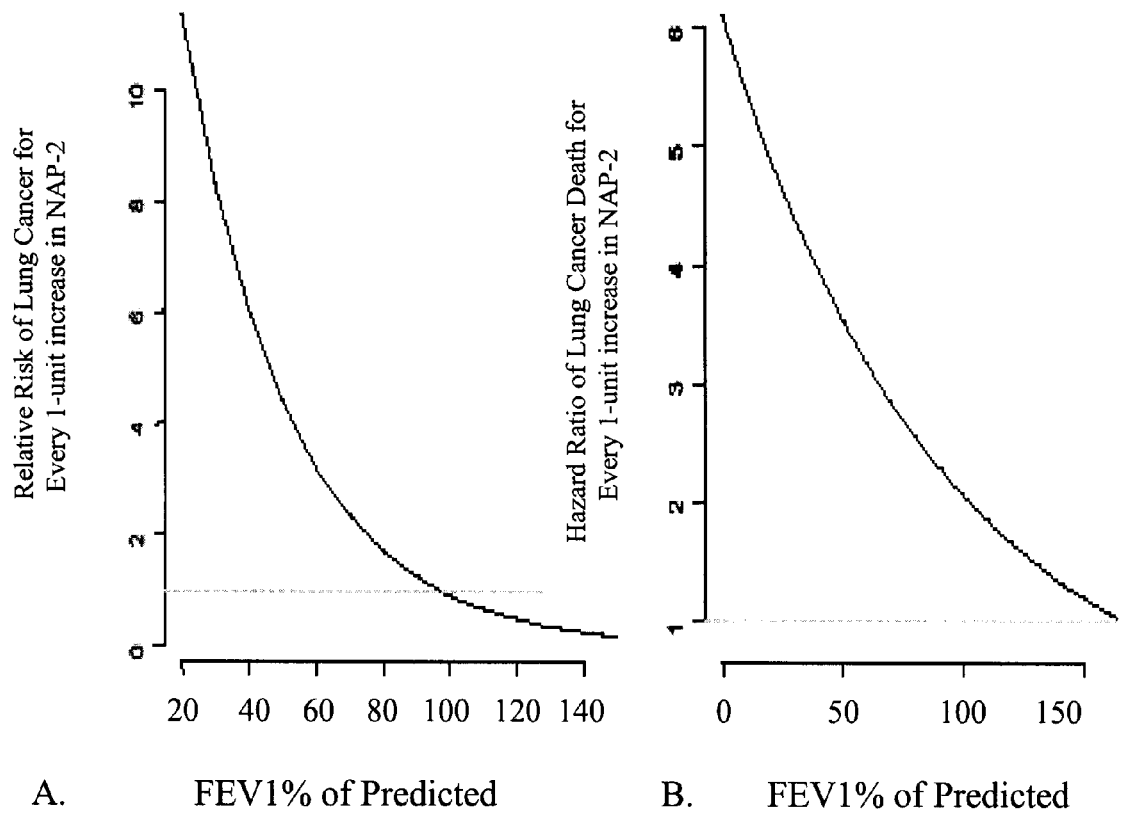
FIG. 5 shows a fitted line illustrating the relationship between the risk of lung cancer and CTAP III/NAP-2 as a function of FEV1%.

FIG. 5 shows a fitted line illustrating the relationship between the risk of lung cancer and CTAP III/NAP-2 as a function of FEV1%. Part A shows data from the BCCA Lung Cancer Prevention Study, while Part B shows data from the NHLBI (National Heart Lung and Blood Institute) Lung Health Study.

The relative risk or hazard ratio of lung cancer is shown for every 1-unit increase in CTAP III/NAP-2 expression (in ng/ml-logarithmic scale) as a function of FEV1 (% of predicted). As FEV1% decreases, the risk of lung cancer is amplified for every 1 unit increase in levels of CTAP FEV1% refers to forced expiratory volume in one second adjusted for age, sex, race, and height.

Figure 6A:
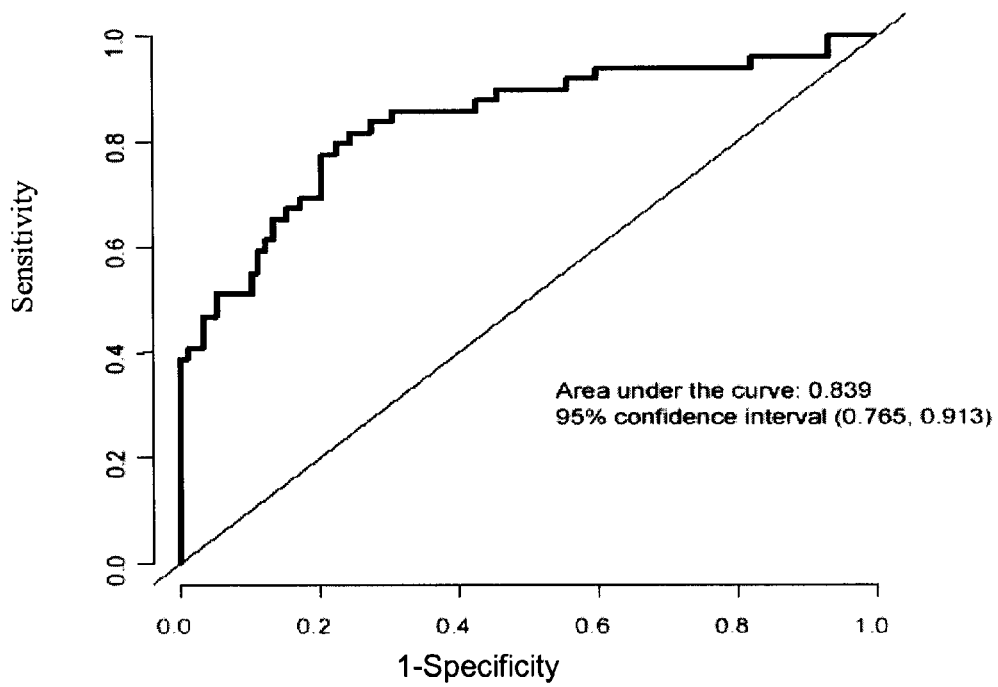
FIG. 6A illustrates the receiver operating characteristics curve (ROC) combining clinical factors and biomarker CTAP III/NAP-2 and haptoglobin in the Lung Cancer Prevention Study.

FIG. 6A illustrates the receiver operating characteristics curve (ROC) combining clinical factors and biomarkers in the Lung Cancer Prevention Study. We have combined Age, Sex, Smoking status, FEV1% (lung function), haptoglobin and CTAP III/NAP-2 together to detect lung Cancer in a high risk population. With an Area under the curve of 0.839, this model is highly predictive.

Figure 6B:
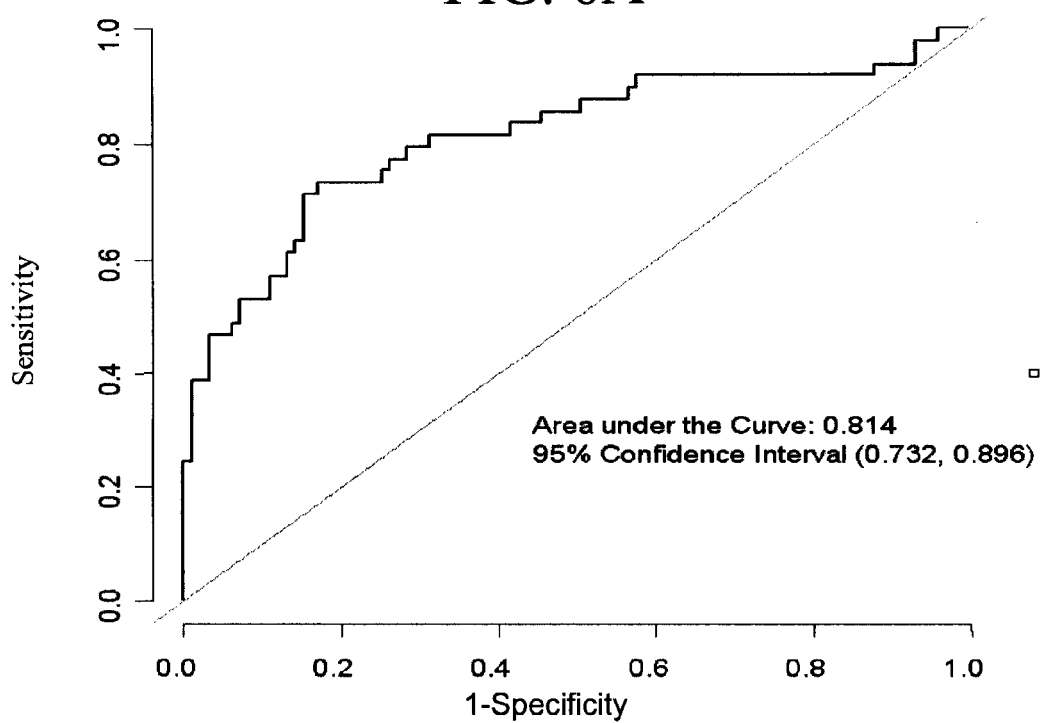
FIG. 6B illustrates the receiver operating characteristics curve (ROC) combining clinical factors and biomarker CTAP III/NAP-2i n the Lung Cancer Prevention Study.

FIG. 6B illustrates the receiver operating characteristics curve (ROC) combining clinical factors and biomarkers in the Lung Cancer Prevention Study. Age, Sex, FEV1, CTAP III/NAP-2 together to detect lung Cancer in a high risk population. With an Area under the curve of 0.814, this model is also highly predictive.

FIG. 7 shows the isolation and identification of the protein at 9320 m/z using a preparative 1D gel followed by MS/MS. Part (a) shows SDS-PAGE analysis of the 40% ACN reversed phase fraction from the flow through/pH 9 anion exchange (Fraction 1) of the patient serum sample with the highest intensity for the 9,320 m/z peak. The proteins in the gel were stained using colloidal coomassie. The serum sample corresponds to FIG. 3 venous blood. The arrow head points to the 9 kDa M$_r$ band on the right hand side of the gel that was excised, trypsin digested and analyzed by MS/MS.

FIG. 7, part (b) is a representative MS/MS spectra of the 1724.8 [M+H]$^+$. Identity of the 1724.8 [M+H]$^+$ ion was confirmed as GKEESLDSDLYAELR (SEQ ID NO: 1) from PBPP with a Mascot ion score of 102 and expect value of $1.8 \times 10^{-8}$. Observed b- and y-ion species are indicated involved in the assignment are indicated. MS/MS spectra from 4 ions in the trypsin digest of the 9 kDa M$_r$ band were assigned by Mascot to CTAP III (underlined sequences) with a score of 263. Theoretical Mw: 9291.74 (CTAP III truncated form of PPBP). Sequence:

(SEQ ID NO: 2)
NLAK<u>GKEESLDSDLYAELR</u>CMCIKTTSGIHPKNIQSLEVIGK<u>GTHCNQVE</u>

<u>VIATLK</u>DGR<u>KICLDPDAPR</u>IKKIVQKKLAGDESAD

Figure 8:
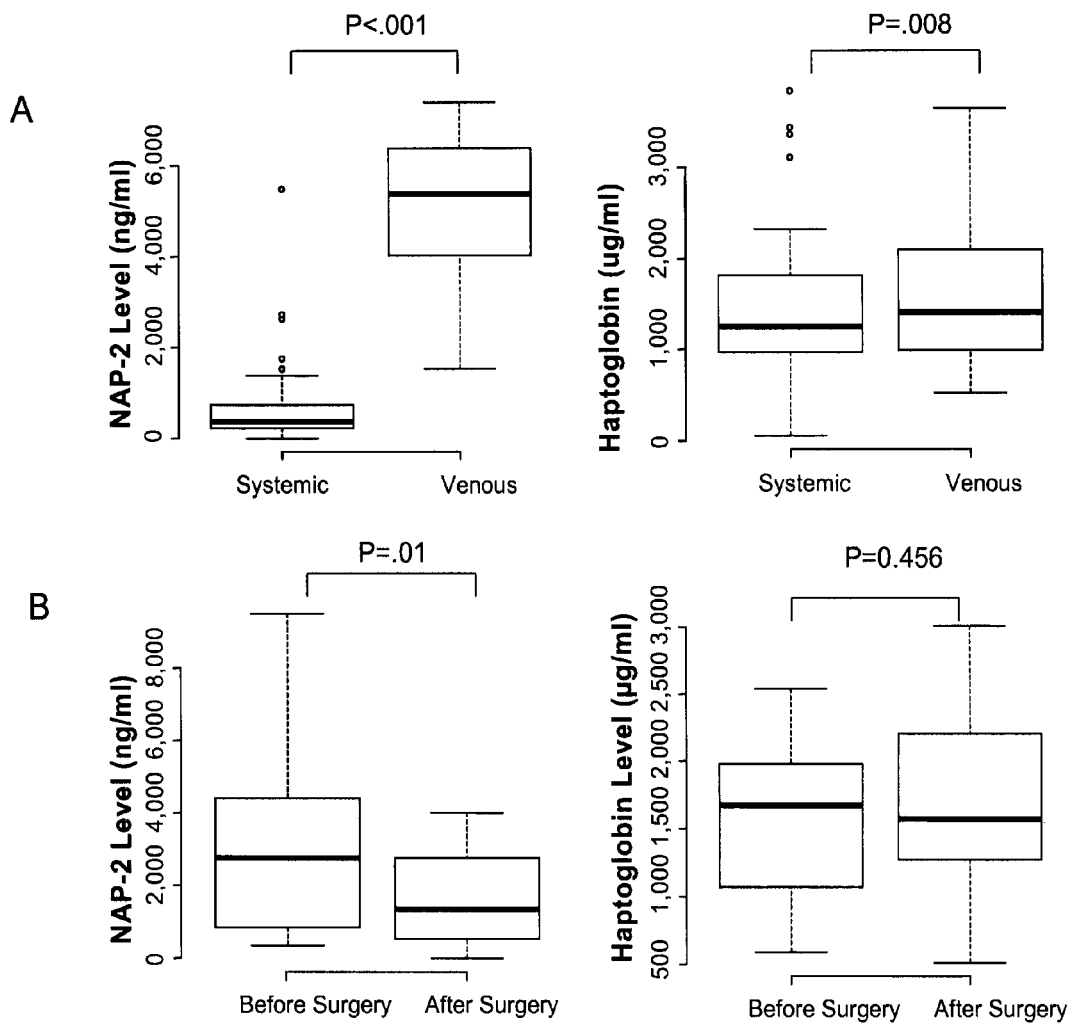
FIG. 8 shows changes in CTAP III/NAP-2 and haptoglobin in systemic and venous blood (top), as well as before and after surgical removal of the tumor (bottom) in 24 patients.

FIG. 8 shows differential protein expression of CTAP III/NAP-2 and haptoglobin between pulmonary venous and systemic blood in 64 patients undergoing thoracotomy for small peripheral lung tumors determined using ELISA. A significantly higher level of CTAP III/NAP-2 was observed in the pulmonary venous blood draining from the tumor (p <0.001). FIG. 8A compares systemic versus venous levels of NAP-2 and haptoglobin. Differences between pulmonary venous and systemic blood in 64 patients undergoing thoracotomy for small peripheral lung tumors. A significantly higher level of CTAP III/NAP-2 and haptoglobin was observed in the pulmonary venous blood draining from the tumor (p <0.001 and p =0.008 respectively). FIG. 8B compares levels before surgery and after surgery. Changes in CTAP III/NAP-2 and haptoglobin, before and after surgical removal of the tumor in 24 patients is observed. A significantly lower level of CTAP III/NAP-2 was observed after tumor removal (p=0.01). The level of haptoglobin level did not change significantly after surgery (p=0.456 ). Biomarker levels in peripheral venous plasma samples of subjects who did and did not develop lung cancer, observed in a Lung Cancer Prevention Study. Only levels of CTAP III/NAP-2 and haptoglobin were significantly higher in plasma of subjects who developed lung cancer (p=0.004 and p<0.001 respectively).

Figure 9:
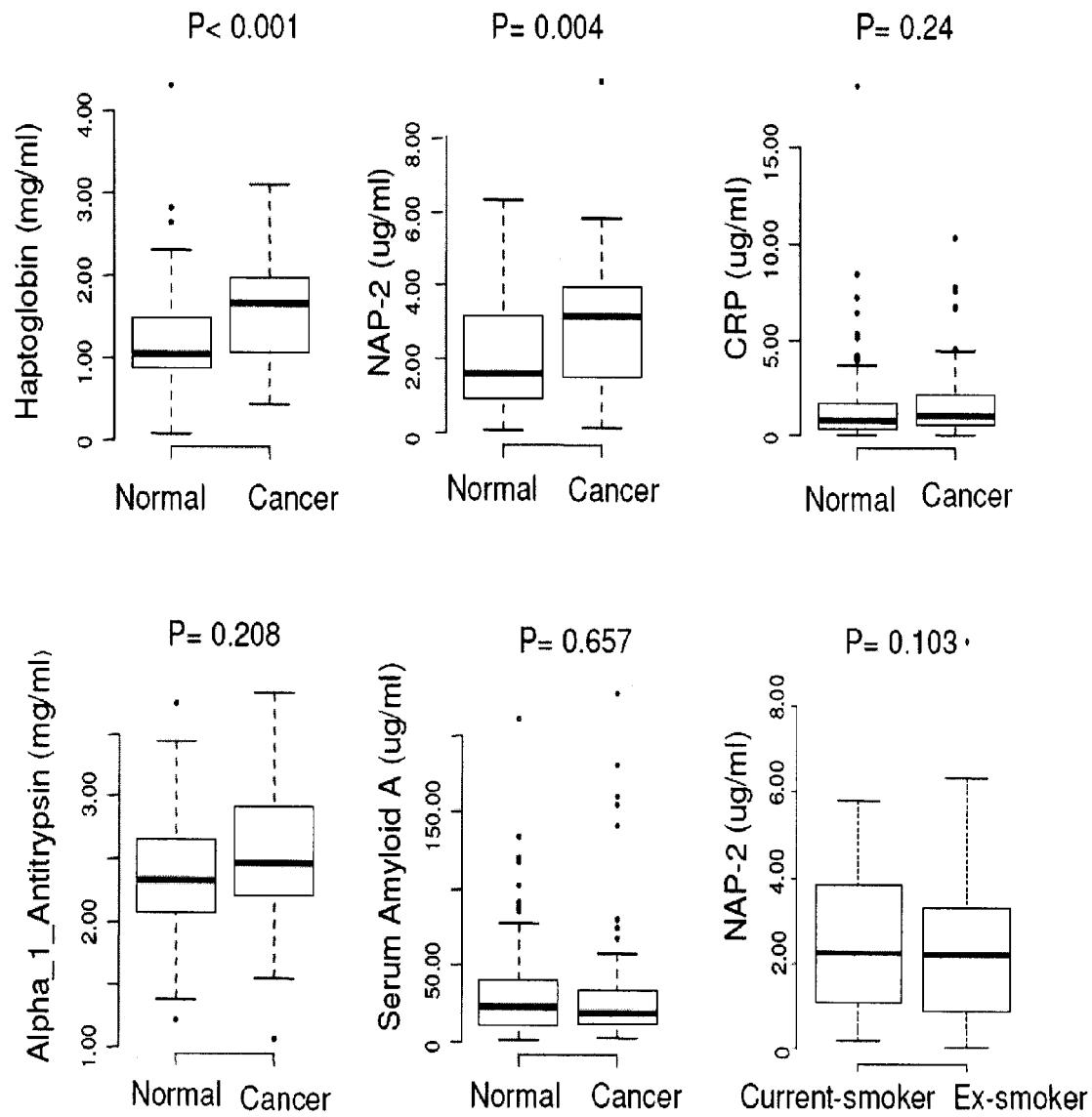
FIG. 9 shows differences in parameters including haptoglobin, CTAP III/NAP-2, CRP, Alpha 1-Antitrypsin, and serum amyloid A in both normal subjects and cancer patients.

FIG. 9 Illustrates differences in blood-based parameters including haptoglobin and CTAP III/NAP-2 levels in either normal subjects or cancer patients. Differences in haptoglobin and CTAP III/NAP-2 are pronounced in haptoglobin and NAP-2 parameters, as compared with other parameters. Biomarker levels in peripheral venous plasma samples of subjects who did and did not develop lung cancer in a lung cancer prevention study are shown. Among various parameters evaluated, only levels of CTAP III/NAP-2 and haptoglobin were significantly higher in plasma of subjects who developed lung cancer (p=0.004 and p<0.001 respectively). The levels of acute phase reactants such as CRP, alpha-1-antitrypsin and serum amyloid A levels were not significantly different between the two groups.

In the final chart of FIG. 9, CTAP III/NAP-2 levels between current and former smokers shows no significant difference between the two groups (p=0.103).

Figure 10:
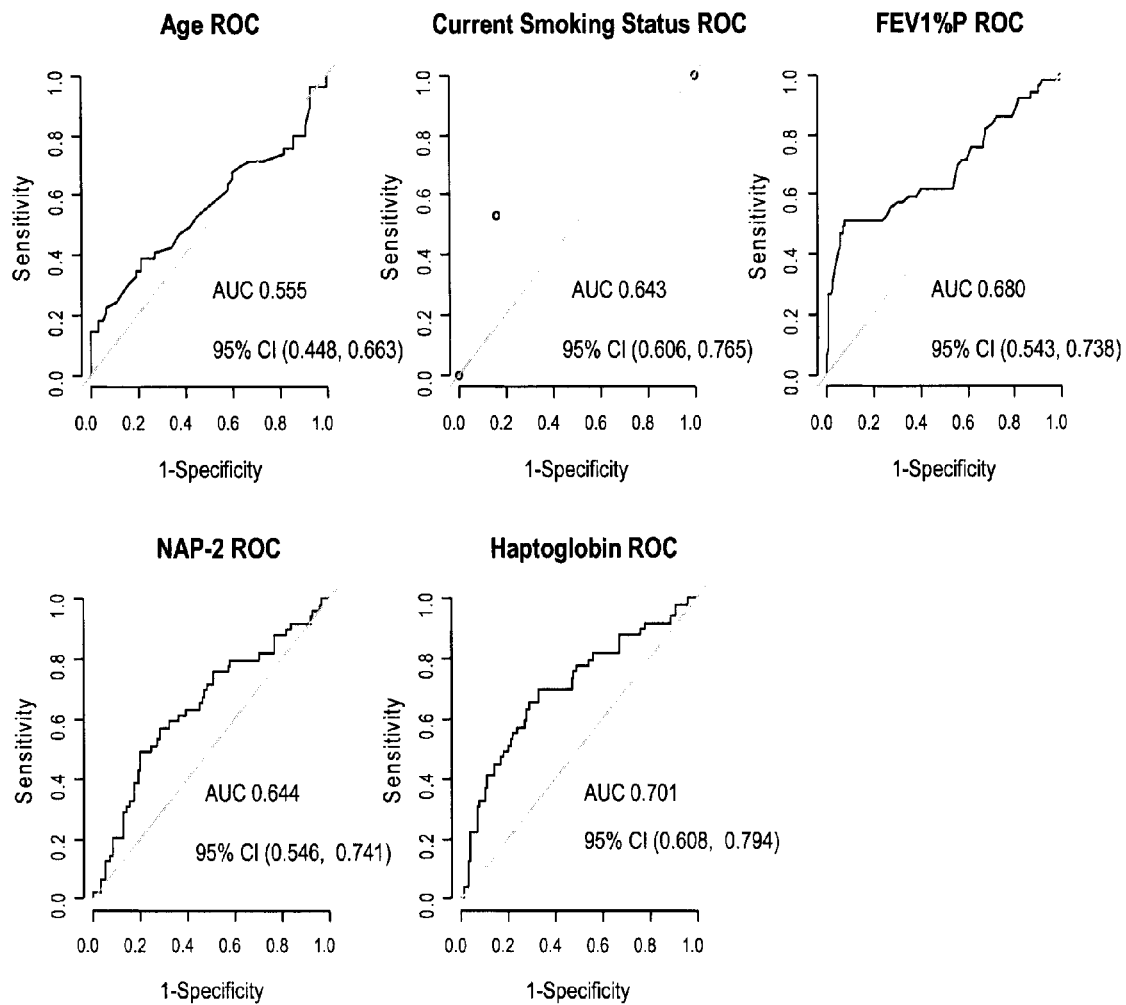
FIG. 10 shows Receiver Operating Characteristics Curves for age, current smoking status, FEV1%, NAP-2, and haptoglobin

FIG. 10 shows Receiver Operating Characteristics Curves of specific clinical factors and biomarkers, namely: age, current smoking status, FEV1%, NAP-2, and haptoglobin.

Figure 11:
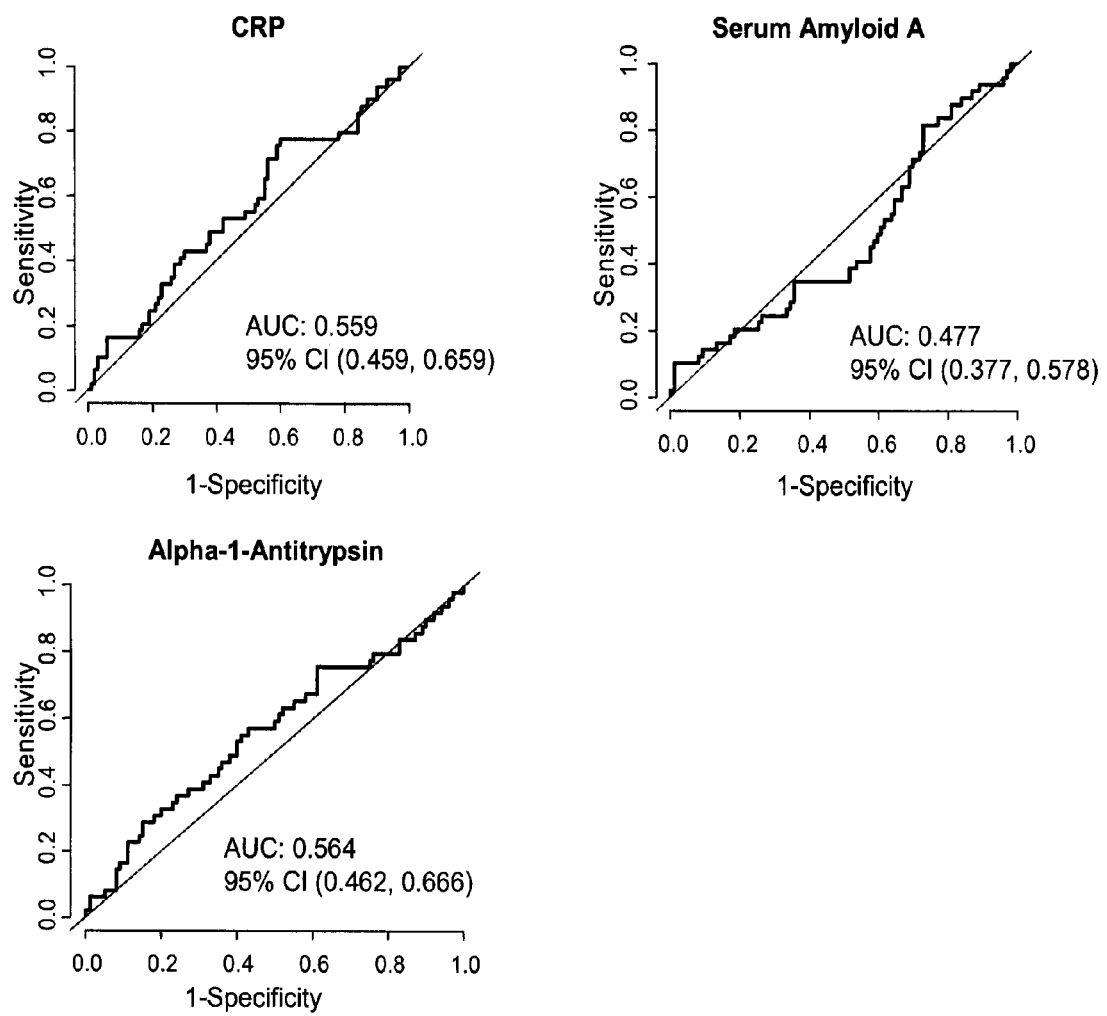
FIG. 11 shows Receiver Operating Characteristics Curves for CPR, Serum Amyloid A, and Alpha-1-antitrypsin.

FIG. 11 shows Receiver Operating Characteristics Curves of specific clinical factors and biomarkers, namely: CPR, Serum Amyloid A, and Alpha-1-antitrypsin.

Figure 12:
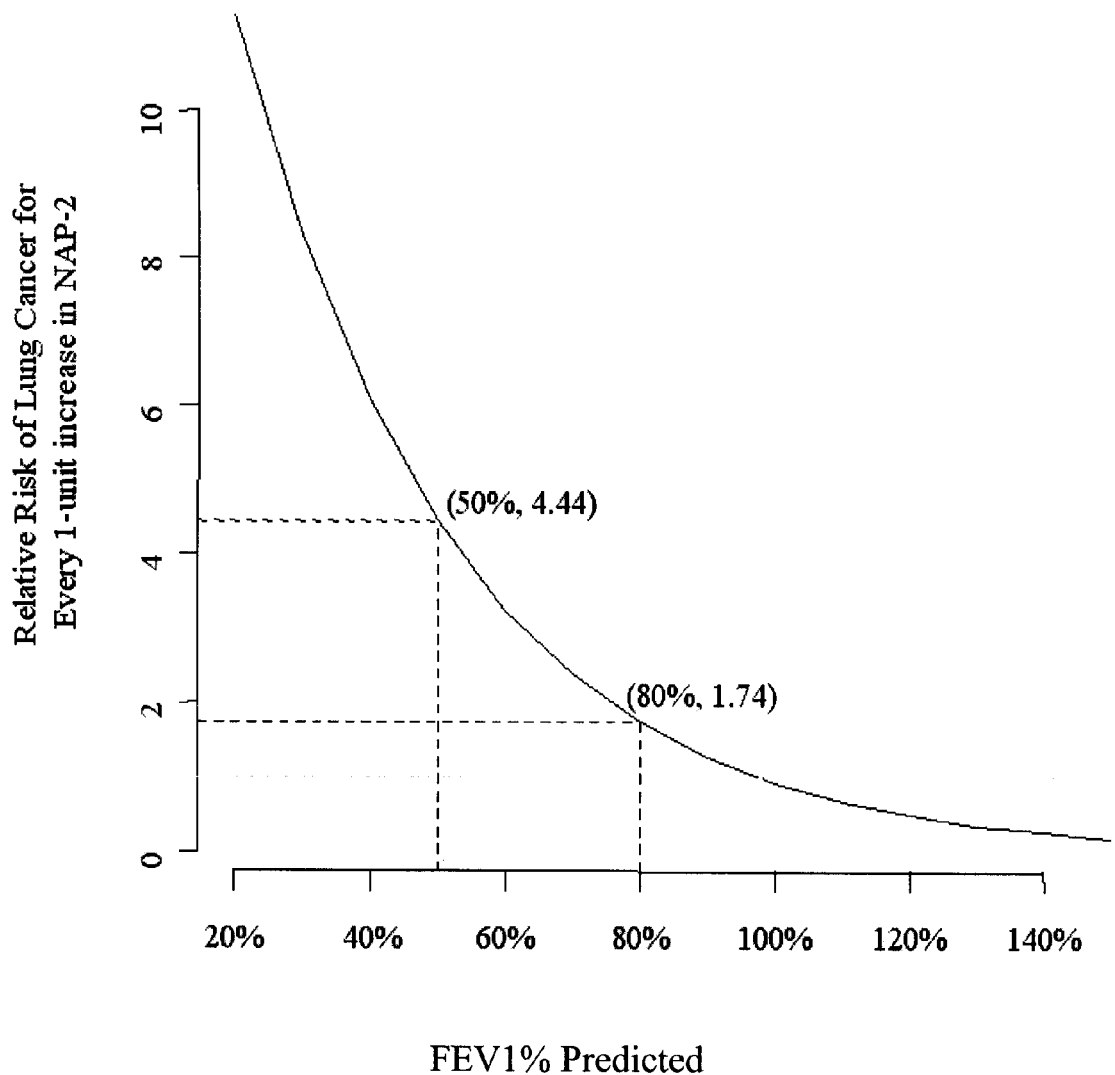
FIG. 12 shows the effect of 1 log-unit (ng/ml) increase in CTAP III/NAP-2 on lung cancer risk.

FIG. 12 shows the effect of 1 log-unit (ng/ml) increase in CTAP III/NAP-2 on lung cancer risk. Interaction with FEV1% is shown.

Figure 13:
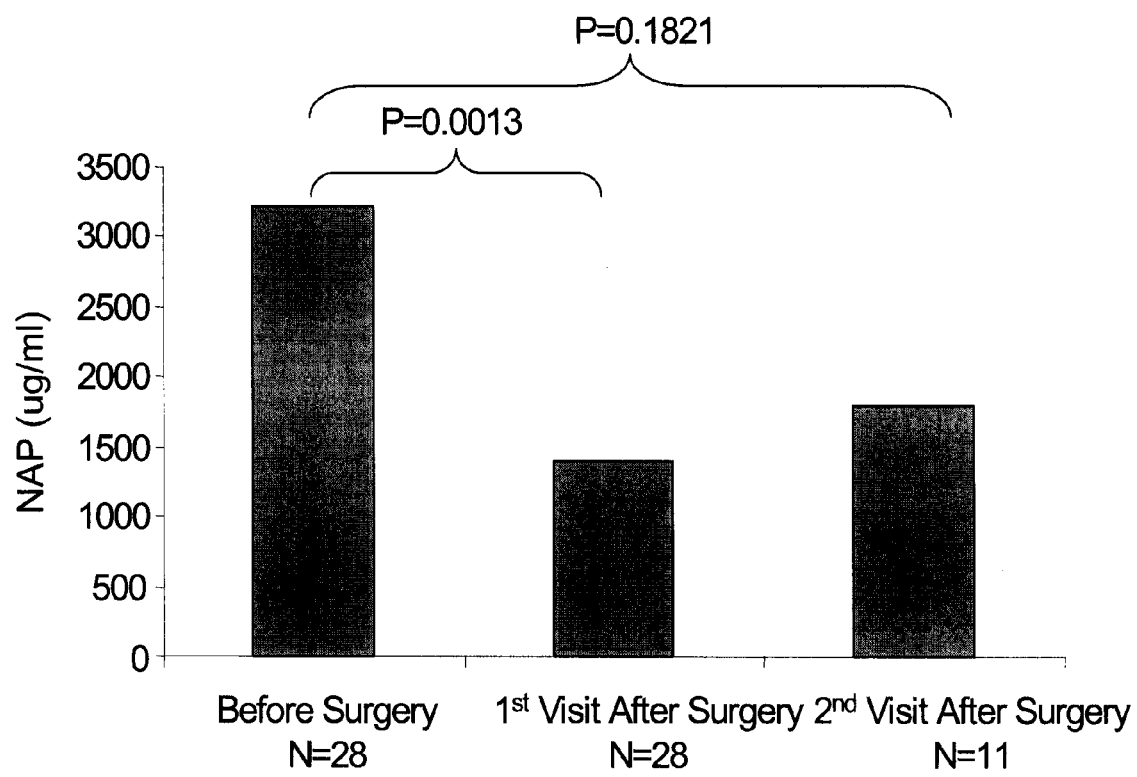
FIG. 13 shows geometric mean of NAP-2 before and after surgery.

FIG. 13 shows geometric mean of CTAP III/NAP-2 before and after surgery. A highly significant difference before and after surgery is seen in the group experiencing no recurrence. The difference in CTAP III/NAP-2 values after surgery is distinctly noted between the groups having recurrence versus the group having no recurrence (P=0.0295).

Figure 14:
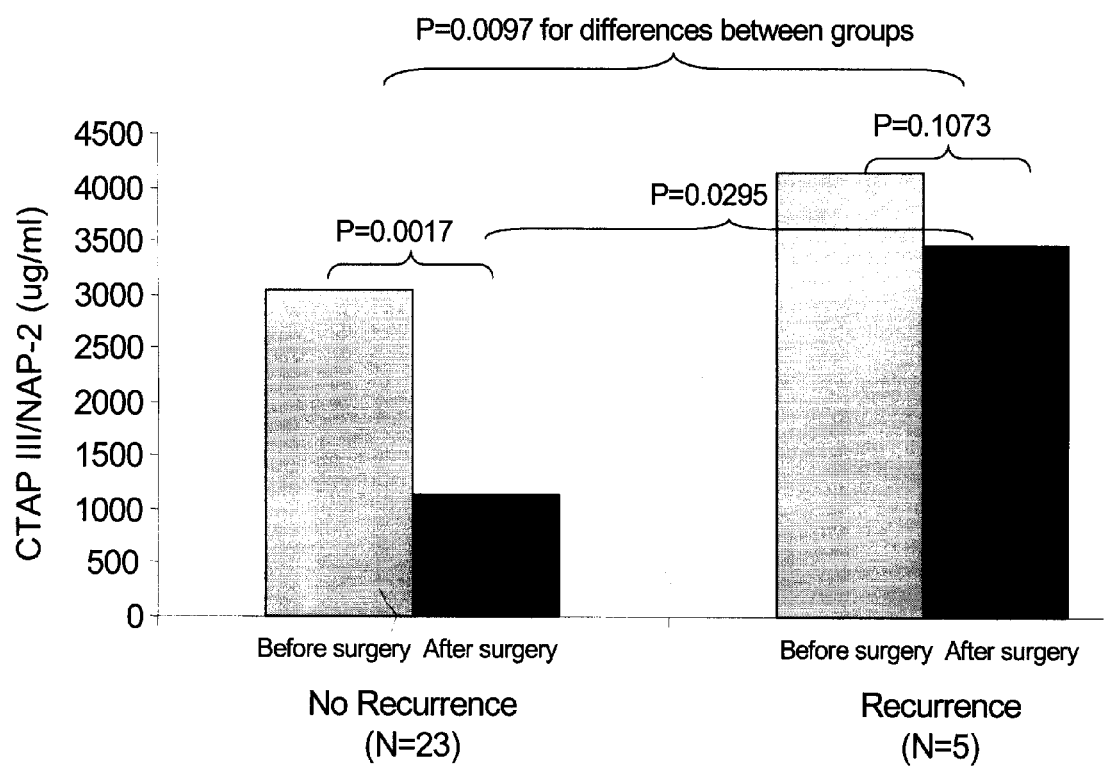
FIG. 14 shows the geometric Mean of CTAP III/NAP-2 before and after surgery stratified by tumor recurrence.

FIG. 14 shows the geometric Mean of NAP-2 before and after surgery stratified by tumor recurrence. Changes in CTAP III/NAP-2 before and after surgical removal of the tumor is shown in 28 patients. A significantly lower level of CTAP III/NAP-2 was observed after tumor removal only in those who did not have tumor recurrence following surgery.

Identification of the 9,320 m/z Protein

The serum sample chosen for enrichment and identification of the 9,320 m/z peak was from the patient with the highest peak intensity in the venous sample to maximize our abilities of protein identification. The sample corresponded to FIG. 3. Anion exchange Fraction 1 was prepared from 200 μl of serum and subjected to hydrophobic fractionation using reversed phase resin. The maximum signal intensity of the 9,320 m/z peak was observed by SELDI-TOF-MS analysis, using an NP20 ProteinChip™ array, in the 40% ACN, 0.1% TFA fraction. Following vacuum concentration to dryness, the reconstituted sample was analyzed by SOS-PAGE (FIG. 7) and a colloidal Coomassie stained band was observed with a relative mobility ($M_r$) of approximately 9 kDa. The intact mass of this band was confirmed to be the 9,320 m/z peak by passively eluting the protein from a portion of the band and confirming its mass by SELDI-TOF-MS analysis on a PBSIIc using an NP20 ProteinChip™ array. The remainder of the protein band, plus a blank region at the edge of the gel were excised and subjected to in gel trypsin digestion and tandem MS/MS analysis using a Qstar™ XL equipped with SELDI ionization source. A Mascot™ MS/MS query of all 4 MS/MS spectra from the top four most intense ions (1724.8, 1583.8, 1198.6, and 1070.5 $[M+H]^+$) was performed against the IPI Human database with a significance threshold of p<0.01. All 4 MS/MS spectra were assigned to four peptides contained in the C-terminal portion of the mature chain of pro-platelet basic protein (PPBP) (Uniprot P02775). Taking into consideration the observed 9320 m/z which corresponded to CTAP III, the 85 amino acids truncation of PBPP, there was 46% sequence coverage (FIG. 7). Further confirmation of protein identification was provided by manual validation of all MS/MS peptide assignments.

Haptoglobin/HPT/P00738 (20,996 m/z) was also identified by LC-MS/MS in a trypsin digest of a 20 kDa $M_r$ band from Fraction 1 of a patient's venous sample who had the highest intensity by similar methods.

Differences in CTAP III/NAP-2 and haptoglobin in pulmonary venous versus systemic blood of lung cancer patients. Upon identification of CTAP III/NAP-2 and haptoglobin by MS/MS from the initial 16 paired venous-arterial sera, we determined the concentrations of these proteins in paired venous-arterial blood samples from 64 patients (Table 1) using ELISA. CTAP III/NAP-2 levels were significantly higher in the pulmonary venous blood compared to systemic blood (p<0.001) (FIG. 8). The median difference in CTAP III/NAP-2 between the pulmonary venous and the systemic blood was 4.93 ug/ml with an interquartile range (IQR) of 3.42 to 5.74 ug/ml. Haptoglobin levels were also higher in the pulmonary venous compared to systemic blood (P<0.008), but the differences were less than those observed with CTAP III/NAP-2 (FIG. 14). The median difference in haptoglobin levels between the pulmonary venous and systemic blood was 0.32 mg/ml (IQR, −0.09 to 0.60 mg/ml).

Correlation of CTAP III/NAP-2 and haptoglobin in the plasma of lung cancer patients before and after surgical resection. Twenty-eight subjects confirmed to have lung cancer (Table 1) had plasma samples collected before and after surgical resection. Levels of CTAP III/NAP-2 decreased significantly after surgery (geometric mean before surgery, 3.22 ug/ml versus after surgery 1.40 ug/ml; a reduction of 57%, p=0.010). Of these 28 patients, 5 experienced a recurrence of lung cancer following surgery. In these individuals, though at the time of blood sampling, recurrence was not known, CTAP III/NAP-2 levels failed to decrease significantly (geometric mean before surgery, 4.14 ug/ml versus after surgery 3.47 μg/ml; p=0.107). In contrast, patients who remained disease-free had significant reduction in plasma NAP-2 levels following surgery compared to pre-surgical levels (pre-surgical geometric mean 3.05 μg/ml versus post-surgical mean 1.15 μg/ml; p=0.002) (FIG. 14). Haptoglobin levels did not change significantly following surgery relative to pre-surgical levels (p=0.46).

CTAP III/NAP-2 and Haptoglobin Levels in Subjects Who Did and Did not Develop Lung Cancer in a Cancer Prevention Study.

Forty-nine subjects participating in the lung cancer prevention cohort were found to have lung cancer in screening studies using low-dose spiral CT and/or autofluorescence bronchoscopy. Of these patients, 47% had Stage 0 or IA non-small cell lung cancer. The clinical characteristics of these subjects and the 100 random controls from the same cohort are shown in Table 2. The median level of CTAP III/NAP-2 in peripheral venous blood was 3.15 μg/ml (IQR of 1.44 to 3.92 μg/ml) in subjects who developed lung cancer, while it was 0.59 pg/ml (IQR, 0.89 to 3.12 μg/ml) for subjects who were free of lung cancer (p=0.004) comparing median levels of CTAP III/NAP-2 between the groups) (FIG. 9). Platelet counts were similar between the two groups (258*89 versus 235±45 giga/L, cancer versus controls, respectively, p=0.092); however, there was a modest correlation between the platelet count and NAP-2 levels (Spearman correlation=0.3; p=0.026). CTAP III/NAP-2 did not vary as a function of the tumor TNM stage (p=0.936), histological cell type or smoking status FIG. 9). There was no significant change in the levels of CTAP III/NAP-2 up to 30 months prior to the diagnosis of lung cancer.

Several biomarkers including haptoglobin were measured for comparison. The median haptoglobin level was 1.66 mg/ml (IQR, 1.08 to 1.97 mg/ml) for subjects who developed lung cancer, while it was 1.06 mg/ml (IQR, 0.86 to 1.48) for subjects who were free of lung cancer (p<0.001 for the two group comparisons). Other biomarkers such as CRP, alpha-1 antitrypsin and SAA were not significantly different between the cancer and non-cancer subjects (FIG. 9).

The fitted logistic regression model demonstrates the relationship between CTAP III/NAP-2 and the risk of lung cancer as a function of the subjects' baseline FEV1 (% predicted) in the lung cancer prevention study. The interaction term between CTAP III/NAP-2 and $FEV_1$ (% predicted) on the risk of lung cancer was negative (coefficient, −0.03) and significant (p=0.009), which indicated that the "effect" of CTAP III/NAP-2 on the risk of lung cancer was amplified as $FEV_1\%$ of predicted decreased (FIG. 5, part A). Plasma haptoglobin was also associated with increased risk of lung cancer (Table 3). In a replication study using the NHLBI LHS samples (Table 4), we found that CTAP III/NAP-2 was significantly associated with lung cancer mortality (p=0.021) when an interaction term was introduced for FEV1% predicted (FIG. 5, part B). Similarly, serum haptoglobin was associated with lung cancer mortality (p=0.016) when an interaction term was introduced for FEV1% predicted.

The receiver operating characteristics (ROC) curves were constructed for the clinical factors and biomarkers (FIG. 10 and FIG. 11). The Area Under Curve (AUC) of the ROC curve for CTAP III/NAP-2 was 0.64 (95% Cl of 0.55 to 0.74) while that for haptoglobin was 0.70 (95% Cl of 0.61 to 0.79). The AUC for the CRP ROC curve was 0.56 (95% Cl, 0.46 to 0.66), and that for SM was 0.48 (95% Cl, 0.38 to 0.58). The AUC of age, smoking status and $FEV_1\%$ predicted combined was 0.80 (95% Cl, 0.72 to 0.88). Inclusion of CTAP III/NAP-2 into this model increased the AUC to 0.81 (95% Cl, 0.73 to 0.89), while inclusion of haptoglobin increased the AUC to 0.82 (95% Cl, 0.74 to 0.90). Simultaneous inclusion of both CTAP III/NAP-2 and haptoglobin plus an interaction term with FEV1% predicted increased the AUC to 0.84 (95% Cl, 0.77 to 0.91) (FIG. 6). Using a threshold of 2.95 µg/ml for CTAP III/NAP-2, the positive predictive value (PPV) was 50.0% while the negative predictive value (NPV) was 77.4%. When. CTAP III/NAP-2, haptoglobin, and other covariates were combined together, the PPV increased to 62.7% and the NPV increased to 88.5%.

Discussion

Application of several mass spectrometry approaches provided an unbiased discovery approach to identify proteins that are elevated after passage through the tumor micro-environment. This led to the discovery of a novel biomarker CTAP III/NAP-2 and a previously reported biomarker haptoglobin as potential biomarkers for detection of lung cancer. Increased levels of CTAP III/NAP-2 in the plasma of smokers who subsequently developed lung cancer were demonstrated in two separate, independent population-based cohorts without a known diagnosis of lung cancer when the blood samples were taken. Elevated blood levels of CTAP III/NAP-2 pre-dated the clinical diagnosis of lung cancer by up to 29 months. Along with clinical characteristics such as age, lung function and smoking status, CTAP III/NAP-2 and haptoglobin can predict the presence of lung cancer with a PPV of 63% and a NPV of 89%. A prospective study to study the incremental benefit of these blood biomarkers as part of a multi-modal lung cancer prediction model to stratify high-risk smokers for lung cancer screening with relatively expensive yet sensitive methods such as low dose spiral CT and autofluorescence bronchoscopy is currently under investigation in a Canada-wide early lung cancer detection study.

Another important finding is a significant decrease in CTAP III/NAP-2 following curative surgical resection but persistence of elevated levels in those who developed recurrent disease following surgery. The potential utility of this biomarker in post-operative surveillance for microscopic residual disease that would lead to clinical recurrence merits further study. A third important finding is the significant interaction between CTAP III/NAP-2 and $FEV_1$. This interaction would have been missed if the biomarkers were evaluated as a stand-alone lung cancer detection test instead of as part of a multi-modal lung cancer risk model. The relationship between the risk of lung cancer and chronic obstructive pulmonary disease has long been recognized[26]. While an inflammatory link between the two diseases that share a common etiology has been hypothesized, this is the first study that shows a significant interaction between CTAP III/NAP-2, decline in lung function ($FEV_1\%$) and lung cancer risk.

CTAP III belongs to the subfamily of ELR+ CXC chemokines that are potent promoters of angiogenesis, tumourigenesis and metastases[27]. Most of the work on the role of CXC chemokines in lung cancer has been on CXCL5 (ENA-78), CXCL8 (IL-8) and CXCL1[28-30]. There is a paucity of information on CXCL7 and lung cancer. Initially, CXCL7 was thought to be expressed only within the megakaryocyte lineage[31,32]. Recent repots suggest other cell types such as monocytes, lymphocytes and neutrophils may produce this chemokine as well[33,34]. CXCL7 has heparanase activity[35]. The very recent finding that pre-malignant breast cancer cells transfected with CXCL7 became as invasive as malignant breast cells suggest an important role of this chemokine in the tumor invasion process[36]. The ability to detect lung cancer at the pre-invasive or early invasive stage is key to success of any early detection program. Of significance is that 47% of the subjects in our validation cohort had Stage 0/IA lung cancer. This is the first report of a blood biomarker that can detect Stage 0 lung cancer.

The lung is a major site of extra-hepatic synthesis of haptoglobin. As a major acute-phase reactant, haptoglobin increases in plasma during inflammation and malignancy such as ovarian cancer[20]. Although haptoglobin was significantly elevated in patients with lung cancer compared with subjects without lung cancer, the levels did not change significantly following surgery suggesting that haptoglobin is a less specific indicator of lung cancer. In the present study, we did not find an association of other acute phase reactants such as serum amyloid A and CRP[11-13,21-23] with lung cancer probably because we performed the tests in population-based cohorts not known to have lung cancer rather than patients with a clinical diagnosis of lung cancer.

In applying our blood biomarkers to early lung cancer detection, we developed a model similar to the highly successful Framingham model to predict cardiovascular disease risk[37]. We combined CTAP III/NAP-2, and haptoglobin along with age, smoking and $FEV_1$ in our risk model and found an area under the curve for lung cancer of 84%. Our study thus underscores the importance of applying blood biomarkers not as a stand-alone test but as part of a multi-modal risk lung cancer prediction model.

In summary, using a novel proteomics discovery approach, we have identified CTAP III/NAP-2 as a potential biomarker in conjunction with demographic and clinical factors to select high-risk ever smokers for lung cancer screening with relatively expensive yet sensitive methods such as low dose spiral CT and autofluorescence bronchoscopy.

In the preceding description, for purposes of explanation, numerous details are set forth in order to provide a thorough understanding of the embodiments of the invention. However, it will be apparent to one skilled in the art that these specific details are not required in order to practice the invention.

The above-described embodiments of the invention are intended to be examples only. Alterations, modifications and variations can be effected to the particular embodiments by those of skill in the art without departing from the scope of the invention, which is defined solely by the claims appended hereto.

All references noted herein are incorporated by reference.

REFERENCES

1. Jemal A, Siegel R, Ward E, et al. Cancer statistics, 2007. CA Cancer J Clin 57, 43-66, 2007.

2. Parkin D M, Bray F, Ferlay J, at al. Global cancer statistics, 2002. CA Cancer J Clin 55:74-108, 2005.
3. Cortese D A, Pairolero P, Bergsralh E, et al. Roentgenographically occult lung cancer. A ten-year experience. J Thorac Cardiovasc Surg 86:373-380, 1983.
4. Rami-Porta R, Ball D, Crowley J, et al. The IASLC Lung Cancer Staging Project: proposals for the revision of the T descriptors in the forthcoming (seventh) edition of the TNM classification for lung cancer. J Thorac Oncol 2:593-602, 2007.
5. Saito Y, Nagamoto N, Ota S, et al. Results of surgical treatment for roentgenographically occult bronchogenic squamous cell carcinoma. J Thorac Cardiovasc Surg 104: 401-407, 1992.
6. Henschke C I, Yankelvitz D, libby D M, et al. Survival of patients with stage I lung cancer detected on CT screening. N Engl J Med 355:1763-1771, 2006.
7. McWilliams A M, Mayo J R, Ahn M I, et al. Lung cancer screening using multi-slice thin-section computed tomography and autofluorescence bronchoscopy. J Thorac Oncol 1: 61-68, 2006.
8. Bach P B, Kattan M W, Thornquist M D, et al. Variations in lung cancer risk among smokers. J Natl Cancer Inst, 95: 470-478, 2003.
9. McWilliams A M, MacAulay C, Gazdar A F, et al. Innovative molecular and imaging approaches for the detection of lung cancer and its precursor lesions. Oncogene 21:6949-6959, 2002.
10. McWilliams A M, Mayo J, MacDonald S, et al. Lung cancer screening: a different paradigm. Am J Respir Crit Care Med, 168:1167-1173, 2003.
11. Gao W M, Kuick R, Orchekowski R P, et al. Distinctive serum protein profiles involving abundant proteins in lung cancer patients based upon antibody microarray analysis. BMC Cancer 5:110, 2005.
12. Khan N, Cromer C J, Campa M, et al. Clinical utility of serum amyloid A and macrophage migration inhibitory factor as serum biomarkers for the detection of nonsmall cell lung carcinoma. Cancer 101: 379-384, 2004.
13. Patz E F Jr, Campa M J, Gottlin E B, et al. Panel of serum biomarkers for the diagnosis of lung cancer. J Clin Oncol 25:5578-5583, 2007.
14. Jacobs J M, Adkins J N, Qian W J, et al. Utilizing human blood plasma for proteomic biomarker discovery. J Proteome Res 4:1073-1085, 2005.
15. Rifai N, Gillette M A, Carr S A. Protein biomarker discovery and validation: the long and uncertain path to clinical utility. Nat Biotechnol 24:971-983, 2006.
16. Anderson N L, Anderson N G. The human plasma proteome: history, character, and diagnostic prospects. Mol Cell Proteomics 1: 845-867, 2002.
17. Anthonisen N R, Skeans M A, Wise R A, et al. The effects of a smoking cessation intervention on 14.5-year mortality: a randomized clinical trial. Ann Intern Med 142:233-239; 2005.
18. Man S F, Connett J E, Anthonisen N R, et al. C-reactive protein and mortality in mild to moderate chronic obstructive pulmonary disease. Thorax 61:849-853, 2006.
19. Rothman K J, Greenland S. Modern Epidemiology. Lippincott-Raven Publishers, 1998.
20. Ahmed N, Barker G, Oliver K T, et al. Proteomic-based identification of haptoglobin-1 precursor as a novel circulating biomarker of ovarian cancer. Br J Cancer 91:129-140, 2004.
21. Benson M D, Eyanson S, Fineberg N S. Serum amyloid A in carcinoma of the lung. Cancer 57:1783-1787, 1986.
22. Liu D H, Wang X M, Zhang L J, et al. Serum amyloid A protein: a potential biomarker correlated with clinical stage of lung cancer. Biomed Environ Sci, 20: 33-40, 2007.
23. Yiidiz P B, Shyr Y, Rahman J S M, et al. Diagnostic accuracy of MALDI mass spectrometric analysis of unfractionated serum in lung cancer. J Thorac Oncol 2:893-901, 2007.
24. Yang S Y, Xiao X Y, Zhang W G, et al. Application of serum SELDI proteomic patterns in diagnosis of lung cancer. BMC Cancer 5: 83, 2005.
25. Prentice R L, Kalbfleisch J D, Peterson A V Jr, et al. The analysis of failure times in the presence of competing risks. Biometrics 34: 541-554, 1978.
26. Wasswa-Kintu S, Gan W Q, Man S F, et al. Relationship between reduced forced expiratory volume in one second and the risk of lung cancer: a systematic review and meta-analysis. Thorax 60:570-575, 2005.
27. Strieter R M, Burdick M D, Mestas J et al. Cancer CXC chemokine networks and tumour angiogenesis. Eur J Cancer 42:768-778, 2006.
28. Zhong L, Roybal J, Chaerkady R, at al. Identification of secreted proteins that mediate cell-cell interactions in an in vitro model of the lung cancer microenvironment. Cancer Res 68:7237-45, 2008.
29. Arenberg D A, Keane M P, DiGiovine B et al. Epithelial-neutrophil activating peptide (ENA-78) is an important angiogenic factor in non-small cell lung cancer. J Clin Invest 102:465-72, 1998.
30. Chen J J, Yao P L, Yuan A, at al. Up-regulation of tumor interleukin-8 expression by infiltrating macrophages: its correlation with tumor angiogenesis and patient survival in non-small cell lung cancer. Clin Cancer Res 9:729-37, 2003.
31. Gewirtz A M, Zhang J, Ratajczak J, et al. Chemokine regulation of human megakaryocytopoiesis. Blood 86:2559-2567, 1995.
32. Brandt E, Ludwig A, Petersen F, et al. Platelet-derived CXC chemokines: Old players in new games. Immunol Rev 177:204-16, 2000.
33. Iida N, Haisa M, Igarashi A, et al. Leukocyte-derived growth factor links the PDGF and CXC chemokine families of peptides. FASEB J 10:1336-1345, 1996.
34. Pillai M M, Iwata M, Awaya N, et al. Monocyte-derived CXCL7 peptides in the marrow microenvironment. Blood 107:3520-3526, 2006.
35. Hoogewerf A J, Leone J W, Reardon I M at al. CXC chemokines connective tissue activating peptide-III and neutrophil activating peptide-2 are heparin/heparan sulfate-degrading enzyme. J Biol Chem 3268-77, 1995.
36. Tang Z, Yu M, Miller F, et al. Increased invasion through basement membrane by CXCL7-transfected breast cells. Am J Surg 196:690-696, 2008.
37. Kennel W B, McGee D, Gordon T A. General cardiovascular risk profile: the Framingham Study. Am J Cardiol 38:46-51, 1976.
38. Diamond D L, Kimball J R, Krisanaprakornkit S, at al. Detection of beta-defensins secreted by human oral epithelial cells. J Immunol Methods 256: 65-76, 2001.
39. Xiao Z, Jiang X, Beckett M L, et al. Generation of a baculovirus recombinant prostate-specific membrane antigen and its use in the development of a novel protein biochip quantitative immunoassay. Protein Expr Purif 19:12-21, 2000.

40. Le L, Chi K, Tyldesley S, et al. Identification of serum amyloid A as a biomarker to distinguish prostate cancer patients with bone lesions. Clin Chem 51:695-707, 2005.
41. Smith C, Damås J K, Otterdal K, et al. Increased levels of neutrophil-activating peptide-2 in acute coronary syndromes: possible role of platelet-mediated vascular inflammation. J Am Coll Cardiol 48(8)1591-9, 2006.
42. Maheshwari A, Christensen R D, Calhoun D A. ELR+ CXC chemokines in human milk. Cytokine. 24(3):91-102, 2003.

The invention claimed is:

1. A method of assessing and treating lung cancer development comprising:
   detecting connective tissue-activating peptide III (CTAP III)-biomarker in a biological sample from a subject, and administering a lung cancer treatment if an elevated level of CTAP III-biomarker, compared with a control, is detected,
   wherein the CTAP III-biomarker is CTAP III, and
   wherein the biological sample is blood, serum, plasma, sputum, bronchial brushings, saliva, tissue obtained through biopsy, or urine.

2. The method of claim 1 wherein assessing lung cancer development comprises detecting lung cancer by detecting an elevated level of the CTAP III-biomarker in the biological sample from the subject, wherein the subject is at risk for developing lung cancer, and wherein administering a treatment comprises treating the subject for lung cancer.

3. The method of claim 2 additionally comprising the step of detecting an increased level of haptoglobin.

4. The method of claim 2 wherein the subject is an individual with chronic obstructive pulmonary disease (COPD), a smoker, or an individual with compromised lung function.

5. The method of claim 2 wherein the level of CTAP III-biomarker is evaluated against a control sample obtained from the subject.

6. The method of claim 5 wherein the biological sample comprises a subject's venous blood, plasma or serum and the control sample comprises a subject's arterial blood, plasma or serum, and/or wherein the control sample comprises a subject's previously obtained biological sample.

7. The method of claim 1 wherein assessing lung cancer development comprises predicting risk of developing lung cancer in the subject by detecting an elevated level of the CTAP III-biomarker in the biological sample from the subject, and
   wherein administering a treatment comprises administering a clinically acceptable follow-up.

8. The method of claim 7 comprising the step of detecting an increased level of haptoglobin.

9. The method of claim 7 comprising detecting one or more additional clinical, social, or demographic risk factors.

10. The method of claim 9 wherein the clinical, social or demographic risk factors comprise age, sex, smoking history, smoking status, smoking family history, education level, socio-economic status, body mass index, COPD, and lung function.

11. The method of claim 7 wherein the subject is an individual with COPD, a smoker, or an individual with compromised lung function.

12. The method of claim 7 wherein levels of the CTAP III-biomarker are evaluated against a control sample obtained from the subject.

13. The method of claim 12 wherein the biological sample comprises a subject's venous blood, plasma or serum and the control sample comprises a subject's arterial blood, plasma or serum, and/or wherein the control sample comprises a subject's previously obtained biological sample.

14. The method of claim 7 wherein the clinically acceptable follow-up comprises assessment by spiral computed tomography (CT), autofluorescence bronchosocopy (AFB), or optical coherence tomography.

15. A method of claim 1 for monitoring the success of lung cancer treatment with curative intent comprising detecting levels of CTAP III biomarker in a biological sample from a subject undergoing treatment for lung cancer for comparison with the previous level obtained from the subject.

16. The method of claim 15, additionally comprising the step of detecting haptoglobin for comparison with a previous level obtained from the subject.

17. The method of claim 15 wherein the biological sample is blood, serum, plasma, sputum, bronchial brushings, saliva, tissue obtained through biopsy, exhaled breath, or urine.

18. The method of claim 1 wherein the CTAP III-biomarker is detected using an imaging agent comprising an antibody to CTAP III.

* * * * *

SEQUENCE LISTING

```
<160> NUMBER OF SEQ ID NOS: 2

<210> SEQ ID NO 1
<211> LENGTH: 15
<212> TYPE: PRT
<213> ORGANISM: Homo sapiens

<400> SEQUENCE: 1

Gly Lys Glu Glu Ser Leu Asp Ser Asp Leu Tyr Ala Glu Leu Arg
1               5                   10                  15

<210> SEQ ID NO 2
<211> LENGTH: 85
<212> TYPE: PRT
<213> ORGANISM: Homo sapiens

<400> SEQUENCE: 2

Asn Leu Ala Lys Gly Lys Glu Glu Ser Leu Asp Ser Asp Leu Tyr Ala
1               5                   10                  15

Glu Leu Arg Cys Met Cys Ile Lys Thr Thr Ser Gly Ile His Pro Lys
            20                  25                  30

Asn Ile Gln Ser Leu Glu Val Ile Gly Lys Gly Thr His Cys Asn Gln
        35                  40                  45

Val Glu Val Ile Ala Thr Leu Lys Asp Gly Arg Lys Ile Cys Leu Asp
    50                  55                  60

Pro Ala Pro Arg Ile Lys Lys Ile Val Gln Lys Lys Leu Ala Gly
65                  70                  75                  80

Asp Glu Ser Ala Asp
                85
```